United States Patent [19]

Teraji et al.

[11] Patent Number: 4,581,356
[45] Date of Patent: Apr. 8, 1986

[54] TRIAZINE DERIVATIVES, AND PHARMACEUTICAL COMPOSITIONS COMPRISING THE SAME

[75] Inventors: Tsutomu Teraji, Osaka; Youichi Shiokawa, Ibaraki; Kazuo Okumura, Sakai; Yoshinari Sato, Takaishi, all of Japan

[73] Assignee: Fujisawa Pharmaceutical Co., Ltd., Osaka, Japan

[21] Appl. No.: 588,343

[22] Filed: Mar. 12, 1984

[30] Foreign Application Priority Data

Mar. 22, 1983 [GB] United Kingdom ................ 8307831
Apr. 18, 1983 [GB] United Kingdom ................ 8310437

[51] Int. Cl.$^4$ .................. C07D 401/04; C07D 413/04; C07D 417/04; A61K 31/53
[52] U.S. Cl. .................... 514/225; 514/236; 514/237; 514/238; 514/239; 514/242; 544/49; 544/105; 544/182
[58] Field of Search .............. 544/182, 49, 105; 424/249; 514/242, 225, 236, 237, 238, 239

[56] References Cited

U.S. PATENT DOCUMENTS 4,347,359  8/1982  Farge et al. .................. 544/182
4,503,054  3/1985  Brown et al. ................. 544/182

FOREIGN PATENT DOCUMENTS 35333    9/1981  European Pat. Off. .......... 544/182
2391202 12/1978  France .
910624   3/1982  U.S.S.R. .................... 544/182

OTHER PUBLICATIONS

Jochims et al., Chemische Berichte, vol. 109, pp. 154–167, (1976).
Vinot et al., C. R. Acad., SC. Paris, t. 270, pp. 1042–1044, (1970).
Mustafa et al., Chemical Abstracts, vol. 76, p. 34221g, (1972).
Nakayama et al., Journal of Heterocyclic Chemistry, vol. 18, pp. 631–632, (1981).

Primary Examiner—John M. Ford
Attorney, Agent, or Firm—Oblon, Fisher, Spivak, McClelland & Maier

[57] ABSTRACT

New triazine derivatives represented by the formula:

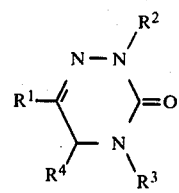

wherein
$R^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, each of which may have one or more substituent(s) selected from lower alkyl, hydroxy(lower)alkyl, lower alkylamino, lower alkanoyl, cyclic lower alkanoyl, lower alkoxy(lower)alkyl, lower alkylamino(lower)alkanoyl, benzyl, benzyloxy(lower)alkyl, lower alkoxycarbonyl(lower)alkyl and 4-(2-hydroxyethyl)piperazin-1-yl-carbonylmethyl;
$R^2$ is a hydrogen, lower alkenyl, benzyl, carboxy(lower)alkyl or lower alkoxycarbonyl(lower)alkyl;
$R^3$ and $R^4$, which may be the same or different, are each hydrogen or lower alkyl or together represent a bond;

provided that when $R^1$ is 2-oxo-1,2,3,4-tetrahydroquinolyl which is unsubstituted or substituted by a lower alkyl, then, $R^4$ is a hydrogen or $R^2$ is a lower alkenyl, benzyl, carboxy(lower)alkyl or lower alkoxycarbonyl(lower)alkyl; and pharmaceutically acceptable salt thereof, which are useful in the treatment of hypertension, thrombosis and ulcer in human beings and animals.

20 Claims, No Drawings

TRIAZINE DERIVATIVES, AND PHARMACEUTICAL COMPOSITIONS COMPRISING THE SAME

The present invention relates to novel triazine derivatives and pharmaceutically acceptable salts thereof. More particularly, it relates to novel, 6-substituted 1,2,4-triazin-3(2H)-one and pharmaceutically acceptable salts thereof which have antihypertensive activity, inhibitory activity on platelet aggregation and antiulcer activity, to processes for preparation thereof, to pharmaceutical composition comprising the same, and to a method of using the same therapeutically in the treatment of hypertension, thrombosis and ulcer in human beings and animals.

Accordingly, one object of this invention is to provide novel 6-substituted-1,2,4-triazin-3(2H)-one and pharmaceutically acceptable salts thereof, which are useful as an antihypertensive agent, antithrombotic agent and antiulcer drug.

Another object of this invention is to provide processes for preparation of said triazine derivatives and pharmaceutically acceptable salts thereof.

A further object of this invention is to provide pharmaceutical composition comprising, as an active ingredient, said triazine derivative or its pharmaceutically acceptable salt.

Still further object of this invention is to provide a method of using said triazine derivative or its pharmaceutically acceptable salt in the treatment of hypertension, thrombosis and ulcer in human beings and animals.

With regard to the state of the arts in this field, for example, the European Patent Publication Number 0052442 describes the following 1,2,4-triazin-3(2H)-one compounds.

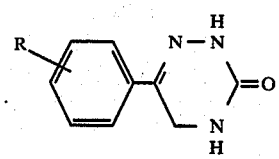

(wherein R is nitro, cyano, amino, methylureido, acetamido, carboxy, lower alkyl, carbamoyl optionally substituted lower alkyl, thiocarbamoyl or morpholinocarbonyl).

It has now been found that certain 6-substituted-1,2,4-triazin-3(2H)-one compounds which have not been described in any of the references have strong antihypertensive activity, inhibitory activity on platelet aggregation and antiulcer activity.

The object compounds of the present invention include the ones represented by the following formula [I].

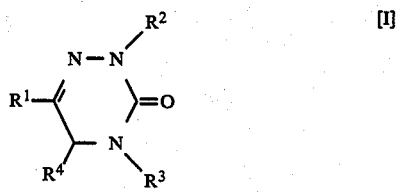

wherein
$R^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which may have one or more substituent(s) selected from lower alkyl, hydroxy(lower)alkyl, lower alkylamino, lower alkanoyl, cyclic lower alkanoyl, lower alkoxy(lower)alkyl, lower alkylamino(lower)alkanoyl, benzyl, benzyloxy(lower)alkyl, lower alkoxycarbonyl(lower)alkyl and 4-(2-hydroxyethyl)piperazin-1-yl-carbonylmethyl;

$R^2$ is a hydrogen, lower alkenyl, benzyl, carboxy(lower)alkyl or lower alkoxycarbonyl(lower)alkyl;

$R^3$ and $R^4$, which may be the same or different, are each hydrogen or lower alkyl or together represent a bond;

provided that when $R^1$ is 2-oxo-1,2,3,4-tetrahydroquinolyl which is unsubstituted or substituted by a lower alkyl, then, $R^4$ is a hydrogen or $R^2$ is a lower alkenyl, benzyl, carboxy(lower)alkyl or lower alkoxycarbonyl(lower)alkyl; and pharmaceutically acceptable salt thereof.

With regard to the object compound [I], it should be understood that the compounds [I] include all of the possible optical and/or geometrical isomers due to the asymmetric carbon atom(s) and/or double bond(s) in their molecules.

Suitable illustrations and examples of the above definitions are explained in the following.

The term "lower" is intended to mean a group having 1 to 6 carbon atoms, unless otherwise indicated.

Suitable "lower alkyl" may include straight or branched lower alkyl such as methyl, ethyl, propyl, isopropyl, butyl, isobutyl, sec-butyl, tert-butyl, pentyl, hexyl and the like, and preferably the ones having 1 to 4 carbon atom(s).

Suitable "hydroxy(lower)alkyl" may include hydroxymethyl, 2-hydroxyethyl, 1-hydroxyethyl, 3-hydroxypropyl, 2-hydroxypropyl, 4-hydroxybutyl, 5-hydroxypentyl, 6-hydroxyethyl and the like.

Suitable "lower alkylamino" may include mono- or di(lower)alkylamino such as methylamino, ethylamino, propylamino, isopropylamino, butylamino, isobutylamino, tert-butylamino, pentylamino, hexylamino, dimethylamino, diethylamino, methylethylamino, dipropylamino, methylpropylamino, dibutylamino, dipentylamino, dihexylamino and the like.

Suitable "lower alkanoyl" may include straight or branched acyclic lower alkanoyl such as formyl, acetyl, propionyl, butyryl, isobutyryl, valeryl, isovaleryl, pivaloyl, hexanoyl and the like, and more preferably the ones having 1 to 4 carbon atom(s).

Suitable "cyclic lower alkanoyl" may include cyclopropanecarbonyl, cyclobutanecarbonyl, cyclopentanecarbonyl, cyclohexanecarbonyl, cycloheptanecarbonyl and the like, and more preferably the ones having 4 to 7 carbon atoms.

Suitable "lower alkoxy(lower)alkyl" may include methoxymethyl, 1-methoxyethyl, 2-methoxyethyl, ethoxymethyl, 2-methoxypropyl, 3-methoxypropyl, 2-ethoxypropyl, 3-ethoxypropyl, isopropoxymethyl, t-butoxymethyl, 4-methoxybutyl, 5-methoxypentyl, 6-methoxyhexyl and the like.

Suitable "lower alkylamino(lower)alkanoyl" may include the aforementioned lower alkanoyl groups being substituted with a mono- or di-(lower alkyl)amino group such as methylamino, dimethylamino, ethylamino, diethylamino, methylethylamino, propylamino, isopropylamino, isiopropylmethylamino, butylamino, pentylamino, hexylamino and the like.

More preferably, "lower alkylamino(lower)alkanoyl" may include methylaminoacetyl, dimethylaminoacetyl, ethylaminoacetyl, diethylaminoacetyl, isopropylaminoacetyl, 3-dimethylaminopropionyl and the like.

Suitable "benzyloxy(lower)alkyl" may include the aforementioned lower alkyl groups being substituted with a benzyloxy group at any carbon of the alkyl group.

More preferably, "benzyloxy(lower)alkyl" may include benzyloxymethyl, 2-benzyloxyethyl, 1-benzyloxypropyl, 2-benzyloxypropyl, 3-benzyloxypropyl, 4-benzyloxybutyl, 5-benzyloxypentyl, 6-benzyloxyhexyl and the like.

Suitable "lower alkoxycarbonyl(lower)alkyl" may include the aforementioned lower alkyl groups being substituted with a lower alkoxycarbonyl group such as methoxycarbonyl, ethoxycarbonyl, propoxycarbonyl, isopropoxycarbonyl, butoxycarbonyl, pentyloxycarbonyl, hexyloxycarbonyl, and the like.

More preferably, "lower alkoxycarbonyl(lower)alkyl" may include methoxycarbonylmethyl, 2-methoxycarbonylethyl, ethoxycarbonylmethyl, 2-ethoxycarbonylethyl, 2-propoxycarbonylethyl, 2-butoxycarbonylethyl and the like.

Suitable "lower alkenyl" may include vinyl, 1-propenyl, allyl, isopropenyl, 1-, 2- or 3-butenyl, 1,3-butadienyl, 3-methyl-2-butenyl, 1-, 2-, 3-, 4- or 5-hexenyl and the like.

Suitable "carboxy(lower)alkyl" may include the aforementioned lower alkyl group being substituted with a carboxy group at any carbon of the alkyl group.

More preferable "carboxy(lower)alkyl" may include carboxymethyl, 2-carboxyethyl, 1-methyl-2-carboxyethyl, carboxybutyl and the like.

"1,2,3,4-Tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, and 3-oxo-2,3-dihydro-4H-1,4-benzoxazinyl" for $R^1$ may have one or more substituent(s) selected from the aforementioned lower alkyl, hydroxy(lower)alkyl, lower alkylamino, lower alkanoyl, cyclic lower alkanoyl, lower alkoxy(lower)alkyl, lower alkylamino(lower)alkanoyl, benzyl, benzyloxy(lower)alkyl, lower alkoxycarbonyl(lower)alkyl and 4-(2-hydroxyethyl)piperazin-1-ylcarbonylmethyl.

Suitable "1,2,3,4-tetrahydroquinolyl" may include 1,2,3,4-tetrahydroquinolin-5 or 6 or 7 or 8-yl compounds.

Suitable "2-oxo-1,2,3,4-tetrahydroquinolyl" may include 2-oxo-1,2,3,4-tetrahydroquinolin-5 or 6 or 7 or 8-yl compounds.

Suitable "2-oxo-1,2-dihydroquinolyl" may include 2-oxo-1,2-dihydroquinolin-5 or 6 or 7 or 8-yl compounds.

Suitable "indolyl" may include 4 or 5 or 6 or 7-indolyl compounds.

Suitable "2-oxoindolinyl" may include 2-oxoindolin-4 or 5 or 6 or 7-yl compounds.

Suitable "benzothiazolyl" may include benzothiazol-4 or 5 or 6 or 7-yl compounds.

Suitable "2-oxobenzothiazolinyl" may include 2-oxobenzothiazolin-4 or 5 or 6 or 7-yl compounds.

Suitable "3,4-dihydro-1H-2,1-benzothiazinyl in which the S atom being optionally oxidized" can be represented as the formula:

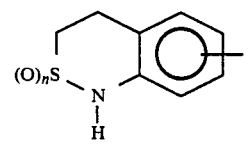

wherein n is an integer of 0 to 2.

Suitable "3-oxo-2,3-dihydro-4H-1,4-benzoxazinyl" may include 3-oxo-2,3-dihydro-4H-1,4-benzoxazin-5 or 6 or 7 or 8-yl compounds.

Suitable pharmaceutically acceptable salts of the object compound [I] are conventional non-toxic salts and may include an acid addition salt such as an inorganic acid addition salt (e.g., chloride, bromide, sulfate, phosphate, etc.), an organic acid addition salt (e.g., oxalate, maleate, lactate, tartrate, fumarate, methanesulfonate, benzenesulfonate, toluenesulfonate, etc.) or a salt with an amino acid (e.g. arginine salt, aspartic acid salt, glutamic acid salt, etc.), a salt with a base such as alkali metal salt (e.g., sodium salt, potassium salt, etc.), alkaline earth metal salt (e.g. calcium salt, magnesium salt, etc.) and the like.

The object compounds [I] of the present invention can be prepared by the following processes.

Process 1

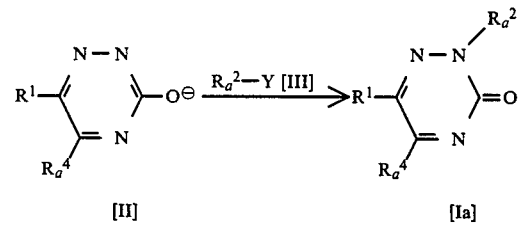

Process 2

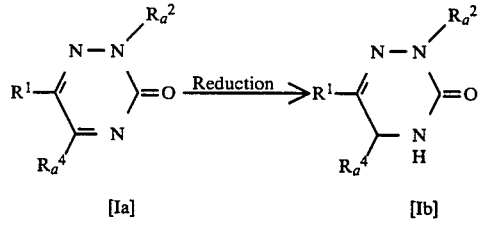

Process 3

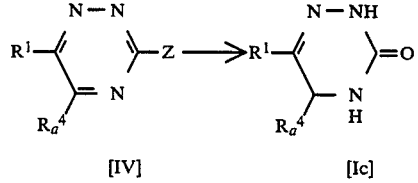

Process 4

-continued

[Id] → [Ie]

Process 5

[If] → [Ig]

Process 6

[Ih] → [Ii]

Process 7

[V] →

[Ij]

Process 8

[VI] →

-continued

[IK]

Process 9

$R^1-COCH_2NHCOOR_a{}^3 \longrightarrow$ [II]

[VII]

Process 10

[Im] → [In]

Process 11

[Im] → [Ip]

Process 12

[Iq] → [Ir]

(wherein $R^1$, $R^2$, $R^3$ and $R^4$ are each as defined above;

$R_a{}^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which has at least one substituent selected from lower alkanoyl, cyclic lower alkanoyl and benzyloxy(lower)alkyl;

$R_b{}^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which may be substituted with a hydroxy(lower)alkyl;

$R_c^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl;

$R_d^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which has at least one substituent selected from lower alkanoyl, cyclic lower alkanoyl, and lower alkylamino(lower)alkanoyl;

$R_e^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which is substituted with a lower alkyl, hydroxy(lower)alkyl, lower alkoxy(lower)alkyl, benzyl, benzyloxy(lower)alkyl, lower alkoxycarbonyl(lower)alkyl and 4-(2-hydroxyethyl)piperazin-1-ylcarbonylmethyl;

$R_f^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which is substituted with a lower alkoxycarbonyl(lower)alkyl;

$R_g^1$ is a 1,2,3,4-tetrahydroquinolyl, 2-oxo-1,2,3,4-tetrahydroquinolyl, 2-oxo-1,2-dihydroquinolyl, indolyl, 2-oxoindolinyl, benzothiazolyl, 2-oxobenzothiazolinyl, 3,4-dihydro-1H-2,1-benzothiazinyl in which the S atom being optionally oxidized, or 3-oxo-2,3-dihydro-4H-1,4-benzoxazinyl, and each of which is substituted with a 4-(2-hydroxyethyl)-piperazin-1-yl-carbonylmethyl;

$R_a^2$ is lower alkenyl, benzyl, carboxy(lower)alkyl or lower alkoxycarbonyl(lower)alkyl;

$R_b^2$ is lower alkoxycarbonyl(lower)alkyl;

$R_c^2$ is carboxy(lower)alkyl;

$R_c^3$ is lower alkyl;

$R_a^4$ is hydrogen or lower alkyl;

$R^5$ is hydrogen or lower alkyl;

$R^6$ is hydrogen or lower alkyl;

$R^7$ is lower alkylamino;

Y is acid residue; and

Z is a leaving group.

Suitable "acid residue" may include halogen (e.g. fluorine, chlorine, bromine, iodine), acyloxy (e.g. benzenesulfonyloxy, tosyloxy, etc.) and the like.

Suitable "leaving group" may include mercapto, lower alkylthio (e.g. methylthio, ethylthio, isopropylthio, etc.), carboxy(lower)alkylthio (e.g. carboxymethylthio, 2-carboxyethylthio, 3-carboxypropylthio, 3-carboxybuthylthio, etc.) and the like.

The other definitions of each symbols are exemplified the ones as described hereinbefore.

PROCESS 1

The compound [Ia] and its salt can be prepared by reacting a compound [II] or its salt with a compound [III] or its salt.

Suitable salt of the compound [II] may be exemplified beforementioned alkali metal salt, alkaline earth metal salt, and the like.

The present reaction is usually carried out in a conventional solvent such as water, alcohol (e.g. methanol, ethanol, isopropyl alcohol, etc.), N,N-dimethylformamide, or any other solvent which does not adversely influence the reaction.

Though the reaction temperature is not critical the reaction may preferably be carried out at ambient temperature or under warming or heating.

The reaction may be conducted in the presence or absence of alkali metal halide (e.g. sodium iodide, potassium iodide, etc.), and the like.

PROCESS 2

The compound [Ib] and its salt can be prepared by reducing a compound [Ia] or its salt.

The reduction can be carried out by a conventional method, for example, by using a reducing agent such as lithium borohydride, sodium borohydride, potassium borohydride, sodium cyanoborohydride or lithium aluminium hydride etc.; by chemical reduction using metal (e.g., zinc, iron, copper, etc.) and acid (e.g., hydrochloric acid, sulfuric acid, etc.) or metal (e.g., sodium, lithium, zinc, etc.) and base (e.g. ammonia, sodium hydroxide, etc.); or by catalytic reduction. The catalytic reduction is usually carried out in the presence of a conventional catalyst, such as Raney nickel, palladium, platinum, rhodium, copper, etc. preferably at ambient temperature under atmospheric pressure and in a conventional solvent. The reduction using a reducing agent is usually carried out in a conventional solvent, preferably a polar solvent, such as water, alcohol, and the like.

The present reaction can be conducted under cooling or slightly elevated temperature, and optionally in the presence of a base such as sodium hydroxide, sodium carbonate, potassium carbonate, etc.

PROCESS 3

The compound [Ic] and its salt can be prepared by treating a compound [IV] or its salt with a base and then reducing the reaction product.

Suitable base to be used in the first step may include alkali metal hydroxide (e.g. sodium hydroxide, potassium hydroxide, etc.), alkaline earth metal hydroxide (e.g. calcium hydroxide, etc.), and the like.

The treatment of the compound [IV] or its salt with a base can be preferably conducted in a polar solvent such as alcohol (e.g., methanol, ethanol, propanol, etc.), water, ether (e.g., dimethyl ether, diethyl ether, tetrahydrofuran, dioxane, etc.), aromatic solvent (e.g., benzene, toluene, xylene, etc.).

The reaction product obtained in the initial step is the compound of the following formula [II] or its salt.

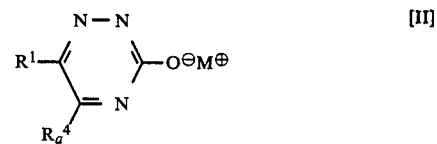
[II]

(wherein $R^1$ and $R_a^4$ are each as defined above, and

M is an alkali metal or alkaline earth metal ion)

Said compound [II] and its salt can be optionally isolated and purified, but they can be used in the second step without isolation or purification, also.

The reduction of the compound [II] or its salt in the second step can be carried out according to a similar manner to that of Process 2.

PROCESS 4

The compound [Ie] and its salt can be prepared by subjecting a compound [Id] or its salt to solvolysis.

The solvolysis is carried out in accordance with a conventional method such as hydrolysis, and the like. Among these methods, hydrolysis in the presence of a base or an acid is one of the common and preferable ones. Suitable base is alkali metal hydroxide, alkaline earth metal hydroxide, or the like.

The present reaction is usually carried out in a solvent such as water, alcohol and the like. The reaction temperature is not critical and the reaction can be carried out at ambient temperature or under warming or heating.

PROCESS 5

The object compound [Ig] and its salt can be prepared by reacting a compound [If] or its salt with an alkylating agent. The preferred alkylating agent may be a lower alkylhalide (e.g., lower alkylchloride, lower alkylbromide, lower alkyliodide), lower alkylsulfate (e.g., dimethylsulfate etc.), lower alkane sulfonate (e.g., lower alkyl mesylate, lower alkyl tosylate etc.) and the like. The reaction is usually carried out in a solvent such as alcohol (e.g., methanol, ethanol, propanol, etc.), at room temperature or under warming, and preferably in the presence of a base such as alkali metal hydroxide (e.g., sodium hydroxide, potassium hydroxide, etc.), alkali metal alkoxide (e.g., sodium methoxide, potassium methoxide, etc.), alkali metal hydride (e.g. sodium hydride, potassium hydride, etc.) and the like.

PROCESS 6

The compound [Ii] and its salt can be prepared by subjecting the compound [Ih] or its salt to an elimination reaction of the protective group. The elimination reaction of the protective group can be conducted by a solvolysis (e.g. hydrolysis, aminolysis, alcoholysis, etc.), hydrogenolysis, or the like according to a kind of the protective group.

Among these methods, in case of the protective group is an acyl group such as a lower alkanoyl, solvolysis in the presence of a base or an acid is one of the common and preferable methods. More preferably, aminolysis using hydrazine or ammonia is convenient.

In case of the protective group is a ar(lower)alkyl group, hydrolysis in the presence of an acid is one of the preferable methods.

Suitable acid may include hydrogen halide (e.g. hydrogen iodide, hydrogen bromide, etc.), boron trihalide (e.g. boron tribromide, boron trichloride, etc.) and the like. The present reaction can be conducted under cooling to heating in a conventional solvent which does not adversely influence the reaction such as water, alcohol, dichloromethane, chloroform and the like.

PROCESS 7

The compound [Ij] and its salt can be prepared by subjecting a compound [V] or its salt to a reaction called "Fischer Indole Synthesis" or chemically equivalent thereto.

Suitable salt of the compound [V] may include a beforementioned alkali metal salt, alkaline earth metal salt and the like.

This reaction is usually carried out in a conventional solvent which does not adversely influence the reaction such as beforementioned alcohol, ethyleneglycohol, benzene, toluene, xylene, and the like. Though the reaction temperature is not critical, the reaction is preferably carried out under warming or heating. The present reaction can optionally be conducted in the presence of a catalyst such as heavy metal halide (e.g. zinc chloride, cuprous chloride, etc.), organic or inorganic acid (e.g., sulfuric acid, hydrochloric acid, acetic acid, etc.) and the like.

PROCESS 8

The compound [Ik] and its salt can be prepared by subjecting a compound [VI] or its salt to a cyclization reaction.

Suitable salt of the compound [VI] may include aforementioned alkali metal salt, alkaline earth metal salt and the like.

The cyclization reaction can be conducted by treating a compound [VI] or its salt with thionyl halide (e.g. thionyl chloride, thionyl bromide, etc.) and then treating the reaction product with an acid (e.g. hydrochloric acid, sulfuric acid, acetic acid etc.) and the like. The present reaction can be conducted in a conventional solvent which does not adversely influence the reaction such as chloroform or aromatic solvent (e.g. benzene, toluene, xylene, etc.) and the like. The reaction temperature is not critical, but the reaction is preferably carried out under warming or heating.

PROCESS 9

The compound [Il] and its salt can be prepared by treating a compound [VII] or its salt with hydrazine hydrate under warming or heating.

This reaction can be carried out in a conventional solvent which does not adversely influence the reaction such as water, aforementioned alcohol, aromatic solvent (e.g. benzene, toluene, xylene etc.), N,N-dimethylformamide and the like.

PROCESS 10

The compound [In] and its salt can be prepared by acylation a compound [Im] or its salt with an acylating agent. The acylating agent is an acid derivative which include an acid halide (e.g. acid chloride, acid bromide, etc.), an acid anhydride such as a mixed acid anhydride with an acid (e.g., phosphoric acid, dialkylphosphorous acid, sulfurous acid, sulfuric acid, alkyl carbonate, aliphatic carboxylic acid, aromatic carboxylic acid, etc.), an activated acid amide with a heterocyclic compound (e.g., imidazole, triazole, etc.), an activated ester (e.g. cyanomethyl ester, 2,4-dinitrophenylester, etc.), isocyanate, isothiocyanate and the like.

The acylation is preferably carried out in the presence of a base in a solvent under cooling or heating according to a conventional way.

Suitable base may include an amine (e.g., triethylamine, pyridine, N,N-dimethylaniline, etc.), an aforementioned alkali metal hydroxide, an alkali metal carbonate (e.g., sodium carbonate, potassium carbonate, etc.), alkali metal bicarbonate (e.g. sodium bicarbonate, etc.), a salt of an organic acid (e.g., sodium acetate, etc.) and the like. In case that the base is liquid, the base can be used as a solvent.

Suitable solvent may include acetonitrile, chloroform, tetrahydrofuran, ethyl acetate, N,N-dimethylformamide, or any other solvent or an optional mixture thereof which does not adversely influence the reaction.

Further, when the acylating agent is used in a form of the free acid or its salt in this reaction, the reaction is preferably carried out in the presence of a conventional condencing agent such as a carbodiimide compound, a ketenimine compound, a phosphorous compound and the like.

PROCESS 11

The compound [Ip] and its salt can be prepared by alkylating a compound [Im] or its salt in a conventional way.

Suitable alkylating agent may be lower alkyl halide such as lower alkyl chloride (e.g., propylchloride, butylchloride, etc.), lower alkyl bromide (e.g., methylbromide, ethylbromide, propylbromide, butylbromide, etc.), lower alkyl iodide (e.g. methyliodide, ethyliodide, propyliodide, etc.); lower alkylsulfate (e.g., dimethylsulfate, diethylsulfate, etc.), lower alkanesulfonate such as lower alkyl mesylate (e.g., methyl mesylate, ethyl mesylate, etc.), lower alkyl tosylate (e.g., methyl tosylate, ethyl tosylate, etc.), a combination of aldehyde or ketone compound and a reducing agent, and the like. Benzyl, Benzyloxy(lower)alkyl, lower alkoxy(lower)alkyl and lower alkoxycarbonyl(lower)alkyl compounds are also obtained by using an alkylating agent having benzyl, benzyloxy, lower alkoxy or lower alkoxycarbonyl group.

Preferred alkylating agent for methylation is a combination of formaldehyde and a reducing agent as mentioned in process 2. The reaction can be conducted in a suitable solvent as mentioned in process 2 at ambient temperature or an elevated temperature in a presence or absence of an acid (e.g., acetic acid, p-toluene sulfonic acid, etc.).

PROCESS 12

The compound [Ir] and its salt can be prepared by reacting a compound [Iq] or its salt with 1-(2-hydroxyethyl)piperazin compound. This reaction can be carried out in a conventional solvent such as alcohol, aromatic solvent, chloroform etc. This reaction can preferably be conducted in the presence of an acid or base mentioned in process 2 above.

The starting compounds of the above processes contain new and known compounds and the new compounds can be prepared by the methods as shown in the Examples or the methods chemically equivalent thereto.

The salts of the starting compounds are exemplified the ones as the salts of compounds [I].

The object compounds [I] obtained in the above Process 1 to 12 can be isolated and purified in a conventional manner, for example, extraction, precipitation, fractional chromatography, fractional crystallization, recrystallization, and the like.

The object compound [I] thus prepared can be transformed into a pharmaceutically acceptable salt by a conventional method, if desired.

In case that the object compound [I] is a mixture of the optical isomers, optical resolution can optionally be conducted by conventional method.

The following antihypertensive testa data, inhibitory activity test data on platelet aggregation and antiulcer test data show that the compound [I] of the present invention exhibit antihypertensive activity, inhibitory activity on platelet aggregation and antiulcer activity, and are useful as antihypertensive agents for treating hypertension and as antithrombotic agents for treating thrombosis and also as antiulcer drugs for treating ulcer in animals and human being.

TEST METHOD A

Five-week old male Wister rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150–200 mmHg were used for experiment between 5 and 7 weeks after surgery.

The test compounds were administered intraperitonealy or orally. Blood pressure was measured at the femoral artery by means of a pressure transducer and recorded as electrically integrated values of mean arterial pressure.

TEST RESULTS A

Mean ratios of maximum decrease of blood pressure (mmHg) were shown in the following table.

| Test Compound (Example No.) | Dose | Effect Max (%) |
|---|---|---|
| 8 - (4) | a | 15 |
| 8 - (4) | b | 49 |
| 10 - (5) | b | 40 |
| 10 - (6) | a | 33 |
| 10 - (6) | b | 57 |
| 12 - (3) | b | 58 |
| 12 - (3) | a | 40 |
| 15 | b | 68 |

*a: The test compound were administered orally in dose of 0.1 mg/kg.
*b: The test compound were administered orally in a dose of 1 mg/kg.

Furthermore, the above mentioned antihypertensive activity of these compounds were observed to continue more than 6 hours.

TEST METHOD B

Platelet rich plasma (PRP) which contains $6.5-7.5 \times 10^8$ platelet/ml was prepared from rabbit blood. To the 200 $\mu$l of PRP, 5 $\mu$l of calcium chloride (1 mM) and 50 $\mu$l of pH 7.4 Tris-acetate solution (5 mM) containing 120 mM NaCl and test compound were added successively, and then stirred for 2 min. at 37° C. To the solution, 5 $\mu$l of adenosine diphosphate (ADP) (2.5 $\mu$M) or collagen (2.5 $\mu$g/ml) was added as an aggregation inducer. Aggregation was measured by using an aggregometer (NKK HEMA TRACER 1). $ID_{50}$ was shown in Table 2.

TEST RESULTS B

| Test Compound (Example No.) | $ID_{50}$ (Mol) ADP | Collagen |
|---|---|---|
| 8 - (4) | $3.6 \times 10^{-7}$ | $2.4 \times 10^{-7}$ |
| 9 - (4) | $4.6 \times 10^{-6}$ | $2.7 \times 10^{-6}$ |
| 10 - (5) | $1.4 \times 10^{-6}$ | $5.4 \times 10^{-7}$ |
| 10 - (6) | $1.3 \times 10^{-6}$ | $4.7 \times 10^{-7}$ |
| 11 - (3) | $3.7 \times 10^{-6}$ | $1.9 \times 10^{-6}$ |
| 11 - (4) | $5.6 \times 10^{-5}$ | $2.2 \times 10^{-5}$ |
| 12 - (3) | $6.7 \times 10^{-8}$ | $4.8 \times 10^{-8}$ |
| 13 | $1.6 \times 10^{-7}$ | $3.4 \times 10^{-8}$ |
| 14 | $2.5 \times 10^{-7}$ | $8.1 \times 10^{-8}$ |

| Test Compound | ID$_{50}$ (Mol) | |
|---|---|---|
| (Example No.) | ADP | Collagen |
| 15 | $5.8 \times 10^{-6}$ | $2.0 \times 10^{-6}$ |

TEST METHODS C

Sprague-Dawley rats weighing about 200 g were used. Each animal was immobilized in a small cage and put in a water bath allowing to respire. The temperature of the water bath kept at 22° C. The test compound was administered orally just before the immobilization. Seven hours later, the animals were sacrificed and their stomachs were removed. The stomach was then fixed with 2% formalin. The area of ulcers was measured for each animal. The mean area (mm$^2$) in the test animals was compared with that in the control animals and inhibition effect (%) were calculated.

TEST RESULTS C

| Test Compound (Example No.) | Dose | Effect (%) |
|---|---|---|
| 8 - (4) | c | 68.0 |
| 8 - (4) | d | 80.0 |

*c: The test compound was administered orally in dose of 10 mg/kg.
*d: The test compound was administered orally in dose of 32 mg/kg.

As being apparent from the above test results, the object compounds [I] of the present invention are useful for antihypertensive medicines, antithrombotic medicines and antiulcer medicines.

The effective ingredient may usually be administered with a dose of 0.01 mg/kg to 500 mg/kg, 1 to 4 times a day in preparations such as tablet, granule, powder, capsule, syrup, injection, suppository and the like. However, the above dosage may be increased or decreased according to the age, weight or conditions of the patient or the administering method.

The pharmaceutical preparation may be prepared in a conventional manner.

The following Examples are given only for the purpose of illustrating the present invention in more detail.

EXAMPLE 1

(1) A mixture of 6-(2-hydroxyiminopropionyl)-1-methyl-2-oxo-1,2,3,4-tetrahydroquinoline (1 g), thiosemicarbazide (0.48 g), methanol (10 ml), water (5 ml) and acetic acid (0.1 ml) was refluxed for 13 hours with stirring. After cooling, the resulting precipitates were collected by filtration, washed successively with ethanol, water and ethanol, and then dried to give 0.34 g of 6-(2-hydroxyimino-1-thiosemicarbazonopropyl)-1-methyl-2-oxo-1,2,3,4-tetrahydroquinoline.

NMR (DMSO-d$_6$, δ): 2.14 (3H, s), 2.4–3.1 (4H, m), 3.25 (3H, s), 7.0–7.3 (3H,m), 8.07 (1H, b.s.), 8.47 (1H, s), 8.5 (1H, b.s.), 11.68 (1H, s).

(2) A mixture of the above obtained compound (5.65 g) of (1) and potassium carbonate (7.35 g) in water (42 ml) was refluxed for 5 hours with stirring. After cooling, the mixture was filtered by suction and then sodium chloroacetate (3.09 g) was added to the filtrate at ambient temperature with stirring. After 15 hours, the mixture was washed with ethyl acetate and then acidified with diluted hydrochloric acid. The resultant precipitates were collected by filtration, washed with water, and dried to give 4.76 g of 3-carboxymethylthio-5-methyl-6-(1-methyl-2-oxo-1,2,3,4-tetrahydroquinolin-6-yl)-1,2,4-triazine.

IR (Nujol): 3050 (broad), 1740, 1645 cm$^{-1}$.

NMR (DMSO-d$_6$, δ): 2.53 (3H, s), Ca. 2.5–2.79 (2H, m), 2.82–3.1 (2H, m), 3.31 (3H, s), 4.11 (2H, s), 7.26 (1H, d, J=8 Hz), 7.59 (1H, d, J=2 Hz), 7.64 (1H, d,d, J=2, 8 Hz).

(3) A solution of potassium hydroxide (13.74 g) in water (36 ml) was added to a solution of the above obtained compound (21.1 g) of Example 1-(2) in methanol (50 ml) and heated at 60° for 4 hours with stirring. The mixture was concentrated to a small volume and cooled. The resultant precipitate was collected by filtration, washed with methanol, and dried in air to give potassium 5-methyl-6-(1-methyl-2-oxo-1,2,3,4-tetrahydroquinolin-6-yl)-1,2,4-triazin-3-oxide (15.07 g).

NMR (DMSO-d$_6$, δ): 2.16 (3H, s), 2.35–3.05 (4H, m) 3.35 (3H,s), 7.10 (1H, d, J=8.5 Hz), 7.26–7.55 (2H, m).

(4) Allyl bromide (1.95 g) was added to a mixture of the above obtained compound (3.4 g) of Example 1-(3) and potassium iodide (1.47 g) in N,N-dimethylformamide (8 ml) and stirred for 60 hours at room temperature. To the mixture was added water and extracted with a mixture of chloroform and methanol. The extract was washed successively with water, an aqueous solution of sodium hydroxide, and water and then purified by column chromatography on silica gel (100 g) with ethyl acetate as an eluent to give 2-allyl-5-methyl-6-(1-methyl-2-oxo-1,2,3,4-tetrahydroquinolin-6-yl)-1,2,4-triazin-3(2H)-one (1.35 g).

The above obtained product (1.34 g) was dissolved in methanol (10 ml) and sodium borohydride (0.16 g) was added to it. After being stirred for 30 minutes at room temperature, the solution was evaporated in vacuo. To the residue was added water and extracted with chloroform. The extract was dried over magnesium sulfate and evaporated in vacuo to give 2-allyl-5-methyl-6-(1-methyl-2-oxo-1,2,3,4-tetrahydroquinolin-6-yl)-4,5-dihydro-1,2,4-triazin-3(2H)-one (1.11 g).

NMR (CDCl$_3$, δ): 1.37 (3H, d, J=6.5 Hz), 2.45–3.17 (4H,m), 3.36 (3H, s), 4.42 (2H,b,d, J=5 Hz), 4.68 (1H, d,q, J=3, 6.5 Hz), 5.07–5.47 (2H, m), 5.68–6.30 (1H, m), 6.44–6.60 (1H, m), 6.97 (1H, d, J=9 Hz), 7.41–7.67 (2H, m).

EXAMPLE 2

(1) A solution of ethyl bromoacetate (2.66 g) in N,N-dimethylformamide (4 ml) was added dropwise to a solution of potassium 5-methyl-6-(1-methyl-2-oxo-1,2,3,4-tetrahydroquinolin-6-yl)-1,2,4-triazin-3-oxide (4.39 g) in the same solvent (28 ml) and stirred for 30 minutes at room temperature. To the solution was added water and extracted with chloroform. The extract was washed with water and chromatographed on silica gel (150 g) with a mixture of ethyl acetate, and benzene (1:1) and then ethyl acetate as eluents. The eluate with ethyl acetate was concentrated to a small volumn. The resultant precipitate was collected by filtration, washed with a mixture of ethyl acetate and diisopropyl ether, and dried to give 2-ethoxycarbonylmethyl5-methyl-6-(1-methyl-2-oxo-1,2,3,4-tetrahydroquinolin-6-yl)1,2,4-triazin-3(2H)-one (1.81 g).

NMR (CDCl$_3$, δ): 1.30 (3H,t, J=7 Hz), 2.53 (3H, s), 2.6–3.2 (4H,m), 3.39 (3H, s), 4.27 (2H, q, J=7 Hz), 4.87 (2H, s), 7.06 (1H, d, J=8 Hz), 7.25–7.56 (2H,m).

(2) Sodium borohydride (0.2 g) was added portionwise to a solution of the above obtained compound (1.8 g) of Example 2-(1) in ethanol (20 ml) under ice cooling.

After being stirred for 30 minutes, the solution was evaporated in vacuo and the residue was acidified with diluted hydrochloric acid under ice cooling. The resultant precipitate was collected by filtration, washed with water, and dissolved in chloroform. The solution was purified by column chromatography on silica gel (30 g) with ethyl acetate as an eluent to give 2-ethoxycarbonylmethyl-5-methyl-6-(1-methyl-2-oxo-1,2,3,4-tetrahydroquinolin-6-yl)-4,5-dihydro-1,2,4-triazin-3(2H)-one (1.19 g).

NMR (CDCl$_3$, δ): 1.29 (3H,t, J=7 Hz), 1.45 (3H, d, J=7 Hz), 2.47–3.16 (4H, m), 3.36 (3H, s), 4.24 (2H, q,J=7 Hz), 4.57 (2H, s), 4.70 (1H, d,q, J=3, 7 Hz), 6.05–6.29 (1H, m), 6.97 (1H, d, J=9 Hz), 7.40–7.66 (2H, m).

(3) A solution of potassium hydroxide (0.35 g) in water (2 ml) was added to a solution of the above obtained compound (1.19 g) of Example 2-(2) in methanol (1 ml) and stirred for 30 minutes at room temperature. To the solution was added dry ice and then evaporated in vacuo. The residue was dissolved in water and the solution was passed through a column of DIAION HP-20 (trade mark, made by Mitsubishi Kasei Co.) (30 ml) and eluted with water and then with a mixture of methanol and water (2:5). The eluate with aqueous methanol was evaporated in vacuo and the oily residue was crystallized from ethanol to give potassium salt of 2-carboxymethyl-5-methyl-6-(1-methyl-2-oxo-1,2,3,4-tetrahydroquinolin-6-yl)-4,5-dihydro-1,2,4-triazin-3(2H)-one (0.52 g), m.p. 300° C. (dec.).

NMR (D$_2$O, δ): 1.32 (3H, d, J=7 Hz), 2.38–3.04(4H, m), 3.26 (3H, s), 4.27 (2H, s), 4.6–4.9 (1H), 6.97–7.17 (1H, d, J=9 Hz), 7.44–7.67 (2H, m).

EXAMPLE 3

(1) A solution of 3-carboxymethylthio-5-methyl-6-(1-methyl-2-oxo-1,2,3,4-tetrahydroquinolin-6-yl)-1,2,4-triazine (7.25 g) in a mixture of 10% aqueous solution of potassium hydroxide (47 ml) and methanol (47 ml) was heated at 60° for 4 hours with stirring. To the mixture were added potassium iodide (0.5 g), benzyl chloride (5.33 g), and methanol (150 ml), refluxed for 8 hours with stirring, and evaporated in vacuo. To the residue was added water and extracted with ethyl acetate. The extract was dried over magnesium sulfate and evaporated in vacuo. The oily residue was purified by column chromatography on silica gel (300 g) with ethyl acetate as an eluent to give 6-(1-methyl-2-oxo-1,2,3,4-tetrahydroquinolin-6-yl)-2-benzyl-5-methyl-1,2,4-triazin-3(2H)-one (4.47 g).

NMR (CDCl$_3$, δ): 2.47 (3H, s), 2.47–3.20 (4H, m), 3.40 (3H, s), 5.31 (2H, s), 6.98–7.65 (8H, m).

(2) 6-(1-Methyl-2-oxo-1,2,3,4-tetrahydroquinolin-6-yl)-2-benzyl-5-methyl-1,2,4-triazin-3(2H)-one (2.21 g) was reacted with sodium borohydride (0.23 g) according to a similar manner to that of Example 2-(2).

The reaction mixture was evaporated in vacuo. To the residue was added 10% hydrochloric acid and extracted with ethyl acetate. The extract was washed with water, dried over magnesium sulfate, and evaporated in vacuo to give 2-benzyl-5-methyl-6-(1-methyl-2-oxo-1,2,3,4-tetrahydroquinolin-6-yl)-4,5-dihydro-1,2,4-triazin-3(2H)-one (2.57 g).

NMR (DMSO-d$_6$, δ): 1.22 (3H, d, J=6.5 Hz), 2.33–3.10 (4H, m), 3.22 (3H, s), 4.69 (1H; q; J=3, 6.5 Hz), 4.86 (2H, s), 6.97–7.43 (7H, m), 7.43–7.70 (2H, m).

(3) Methyl iodide (1.96 g) was added to a mixture of the above obtained compound (2.53 g) of Example 3-(2) and sodium hydride (0.218 g) in N,N-dimethylformamide (3 ml), and heated at 50° for 1 hour with stirring. To the mixture was added water and extracted with ethyl acetate. The extract was dried over magnesium sulfate and evaporated in vacuo. The residue was chromatographed on silica gel (30 g) with ethyl acetate as an eluent. The eluate was evaporated in vacuo and the residual solid was washed successively with diisopropyl ether and ethyl acetate to give 2-benzyl-4,5-dimethyl-6-(1-methyl-2-oxo-1,2,3,4-tetrahydroquinolin-6-yl)-4,5-dihydro-1,2,4-triazin-3(2H)-one (1.39 g).

NMR (CDCl$_3$, δ): 1.32 (3H, d, J=6.7 Hz), 2.45–3.16 (4H, m), 3.04 (3H, s), 3.36 (3H, s), 4.48 (1H, q, J=6.7 Hz), 4.86 (1H, d, J=15 Hz), 5.16 (1H, d, J=15 Hz), 6.96 (1H, d, J=9 Hz), 7.15–7.66 (7H, m).

EXAMPLE 4

(1) 1-(2-Benzyloxyethyl)-2-oxo-6-propionyl-1,2,3,4-tetrahydroquinoline (32.4 g) was dissolved in methylene chloride (97 ml) and the solution was saturated with hydrogen chloride. To the stirred solution was added dropwise iso-amyl nitrite (13.5 g) over 0.5 hour. After stirring for 1 hour, the reaction mixture was evaporated in vacuo and the oily residue was dissolved in diethyl ether and extracted with 10% aqueous solution of sodium hydroxide. The extract was washed with diethyl ether, acidified with diluted hydrochloric acid, and extracted with chloroform. The extract was washed with water, dried over magnesium sulfate, and evaporated in vacuo. The oily residue was triturated with benzene to give 1-(2-benzyloxyethyl)-6-(2-hydroxyiminopropionyl)-2-oxo-1,2,3,4-tetrahydroquinoline (9.19 g).

IR (Nujol): 3250 (shoulder), 3160, 3020, 1640, 1600 cm$^{-1}$.

NMR (CDCl$_3$, δ): 2.15 (3H, s), 2.3–3.1 (4H, m), 3.70 (2H, t, J=5.5 Hz), 4.14 (2H, t, J=5.5 Hz), 4.47 (2H, s), 7.0–7.5 (6H, m), 7.7–8.0 (2H, m), Ca. 10.0 (1H, b.s.).

(2) 1-(2-Benzyloxyethyl)-6-(2-hydroxyimino-1-thiosemicarbazonopropyl)-2-oxo-1,2,3,4-tetrahydroquinoline (8.99 g) (isomeric mixture) was obtained from the above object compound (8.98 g) of Example 4-(1) according to a similar manner to that of Example 1-(1).

IR (Nujol): 3410, 3300, 3160, 1665, 1600 cm$^{-1}$.

NMR (DMSO-d$_6$, δ): 1.96 (s), 2.17 (s) } (3H), Ca. 2.4–3.1 (4H, m), 3.63 (2H, b.t., J = 5Hz), 4.15 (2H; b.t., J = 5Hz), 4.47 (s), 4.50 (s) } (2H), 6.92–7.5 (3H, m), 7.3 (5H, s), Ca. 8.0 (b.s.), 7.66 (b.s.) } (1H), 8.13 (b.s.), 8.54 (b.s.) } (2H), 12.1 (s), 11.69 (s) } (1H)

(3) A mixture of the above obtained compound (10.1 g) of Example 4-(2), potassium carbonate (7.03 g) and water (57 ml) was refluxed for 3.5 hours with stirring, and the reaction mixture was treated with activated charcoal and filtered by suction. To the filtrate was added dropwise methyl iodide (3.91 g) with stirring, and the stirring was continued for 15 minutes at ambient temperature. The reaction mixture was extracted with chloroform. The extract was washed with water, dried over magnesium sulfate, and evaporated in vacuo. The residue was purified by column chromatography on silica gel (60 g) with chloroform as an eluent to give an oil of 6-[1-(2-benzyloxyethyl)-2-oxo-1,2,3,4-tetrahydroquinolin-6-yl]-5-methyl-3-methylthio-1,2,4-triazine (6.81 g).

IR (film/NaCl): 1675, 1610 cm$^{-1}$.

NMR (CDCl$_3$, δ): 2.59 (3H, s), 2.72 (3H, s), Ca. 2.5–3.2 (4H, m), 3.79 (2H, t, J=5.2 Hz), 4.23 (2H, t, J=5.2 Hz), 4.56 (2H, s), 7.29 (5H, s), 7.3–7.7 (3H, m).

(4) A mixture of the above obtained compound (6.62 g) of Example 4-(3) in 10% aqueous solution of potassium hydroxide (33 ml) and methanol (65 ml) was heated at 60° C. for 10.5 hours with stirring and allowed at room temperature. To the solution was added sodium borohydride (0.8 g), stirred for 1.5 hours at room temperature and acidified with conc. hydrochloric acid under ice cooling. After addition of water thereto, the reaction mixture was extracted with chloroform and the extract was washed with water, dried over magnesium sulfate, and evaporated in vacuo. The oily residue was triturated with acetone to give 6-[1-(2-benzyloxyethyl)-2-oxo-1,2,3,4-tetrahydroquinolin-6-yl]-5-methyl-4,5-dihydro-1,2,4-triazin-3(2H)-one (3.92 g).

IR (Nujol): 3220, 3100, 1685, 1645, 1620 cm$^{-1}$.

NMR (DMSO-d$_6$, δ): 1.21 (3H, d, J=6.4 Hz), Ca. 2.4–2.8 (2H, m), 2.8–3.2 (2H, m), 3.62 (2H, t, J=5.4 Hz), 4.13 (2H, t, J=5.4 Hz), 4.48 (2H, s), Ca. 4.4–4.9 (1H, m), Ca. 7.1–7.8 (4H, m), 7.26 (5H, s), 9.93 (1H, d, J=2 Hz).

(5) A solution of boron tribromide (4.59 g) in methylenechloride (5 ml) was added dropwise to a stirred suspension of 6-[1-(2-benzyloxyethyl)-2-oxo-1,2,3,4-tetrahydroquinolin-6-yl]-5-methyl-4,5-dihydro-1,2,4-triazin-3(2H)-one (2.38 g) in methylene chloride (200 ml) at −40° C. over a period of 10 minutes. After being stirred for 40 minutes at the same temperature, methanol (0.6 ml) was added to the suspension and evaporated in vacuo. The residue was dissolved in n-butanol, washed with brine, and evaporated in vacuo. The residual solid was washed with ethyl acetate and recrystallized from methanol to give 6-[1-(2-hydroxyethyl)-2-oxo-1,2,3,4-tetrahydroquinolin-6-yl]-5-methyl-4,5-dihydro-1,2,4-triazin-3(2H)-one (0.91 g), mp 237° to 243° C.

IR (Nujol): 3300, 3200, 1665, 1635, 1620 cm$^{-1}$.

NMR (DMSO-d$_6$, δ): 1.21 (3H, d, J=6.4 Hz), Ca. 2.3–2.4 (2H, m), 2.4–3.1 (2H, m), 3.69 (2H, b.d., J=5.5 Hz), 3.91 (2H, b.d., J=5.5 Hz), 4.64 (1H; d, q; J=3, 6.4 Hz), 7.24 (1H, d, J=9.4 Hz), 7.39 (1H; b.s.), 7.55 (2H, b.s.), 9.91 (1H, d, J=1.6 Hz).

Anal. Calcd. for C$_{15}$H$_{18}$N$_4$O$_3$: C, 59.59; H, 6.00; N, 18.57. Found: C, 59.33; H, 6.02; N, 17.98.

EXAMPLE 5

(1) 6-(2-Hydroxyiminopropionyl)-4-methyl-2,3-dihydro-4H-1,4-benzoxazin-3-one (5.71 g) was obtained from 4-methyl-6-propionyl-2,3-dihydro-4H-1,4-benzoxazin-3-one (10.05 g) according to a similar manner to that of Example 4-(1).

IR (Nujol): 3360, 1670, 1636 cm$^{-1}$.

NMR (DMSO-d$_6$, δ): 2.03 (3H, s), 3.31 (3H, s), 4.75 (2H, s), 7.06 (1H, d, J=9.4 Hz), 7.5–7.74 (2H, m), 12.21 (1H, s).

(2) 6-(2-Hydroxyimino-1-thiosemicarbazonopropyl)-4-methyl-2,3-dihydro-4H-1,4-benzoxazin-3-one (6.28 g) was obtained from the above obtained compound (5.71 g) of Example 5-(1) according to a similar manner to that of Example 1-(1).

IR (Nujol): 3340, 3250, 3160, 1687, 1622 cm$^{-1}$.

NMR (DMSO-d$_6$, δ): 1.94 (s) ⎫ 3.36 (s) ⎫
2.15 (s) ⎬ (3H), 3.25 (s) ⎬ (3H),
4.71 (2H, s), 6.7–7.6 (3H, m), 8.13 (1H, b.s.),
8.62 (2H, b.s.), 12.15 (s) ⎫
11.69 (s) ⎬ (1H)

(3) 6-(4-Methyl-3-oxo-2,3-dihydro-4H-1,4-benzoxazin-6-yl)-5-methyl-3-methylthio-1,2,4-triazine (2.1 g) was obtained from the above obtained compound (6.28 g) of Example 5-(2) according to a similar manner to that of Example 4-(3).

IR (Nujol): 1678 cm$^{-1}$.

NMR (DMSO-d$_6$, δ): 2.52 (3H, s), 2.66 (3H, s), 3.32 (3H, s), 4.73 (2H, s), 7.0–7.5 (3H, m).

(4) 6-(4-Methyl-3-oxo-2,3-dihydro-4H-1,4-benzoxazin-6-yl)-5-methyl-4,5-dihydro-1,2,4-triazin-3(2H)-one (0.79 g) was obtained from the above obtained compound (2.1 g) of Example 5-(3) according to a similar manner to that of Example 4-(4).

mp: 286° to 290° C. (recrystallized from 70% aqueous ethanol).

NMR (DMSO-d$_6$, δ): 1.22 (3H, d, J=6.8 Hz), 3.32 (3H, s), 4.68 (1H, m), 4.71 (2H, s), 7.03 (1H, d, J=8.2 Hz), 7.2–7.6 (3H, m), 9.96 (1H, b.s.).

IR (Nujol): 3250, 3050, 1696, 1661 cm$^{-1}$.

Anal. Calcd. for C$_{13}$H$_{14}$N$_4$O$_3$: C, 56.93; H, 5.14; N, 20.43. Found: C, 57.19; H, 5.13; N, 20.56.

EXAMPLE 6

(1) An isomeric mixture of 4'-acetylamino-2-hydroxyiminopropiophenone thiosemicarbazone (1.7 g) was obtained from 4'-acetylamino-2-hydroxyiminopropiophenone (1.87 g) according to a similar manner to that of Example 1-(1).

NMR (DMSO-$_6$, δ): 2.08 (3H, s), 2.17 (3H, s),
7.18 (2H, d, J = 8Hz), 7.73 (2H, d, J = 8Hz),
8.13 (1H, b.s.), 8.63 (2H, b.s.),
9.10 (b.s.) ⎫ 11.69 (s) ⎫
10.23 (b.s.) ⎬ (1H), 12.26 (s) ⎬ (1H)

(2) A mixture of the above object compound (34.74 g) of the Example 6-(1) and potassium carbonate (35.88 g) in water (300 ml) was refluxed for 3 hours under stirring. After cooling, sodium chloroacetate (20.6 g) was added to the solution at ambient temperature and stirring was continued for 2 hours. The aqueous solution was washed with chloroform, acidified with hydrochloric acid, and allowed to stand over night in a refrigerator. The precipitates were collected by filtration, washed with water and dried to give 6-(4-acetylaminophenyl)-3-carboxymethylthio-5-methyl-1,2,4-triazine (16.7 g).

NMR (DMSO-d$_6$, δ): 2.10 (3H, s), Ca. 2.5 (3H, s), 3.96 (2H, s), 7.58 (2H, d, J=8 Hz), 7.77 (2H, d, J=8 Hz), 10.35 (1H, s).

(3) 6-(4-Acetylaminophenyl)-5-methyl-4,5-dihydro-1,2,4-triazin-3(2H)-one (6.12 g) was obtained from the above object compound (10.61 g) of Example 6-(2) according to a similar manner to that of Example 4-(4).

mp: 272° to 273° C. (recrystallized from 60% ethanol).

NMR (DMSO-d$_6$, δ): 1.22 (3H, d, J=7 Hz), 2.08 (3H, s), 4.64 (1H, m), 7.43 (1H, b.s.), 7.68 (4H, s), 9.96 (1H, d, J=2 Hz), 10.10 (1H, s).

Anal. Calcd. for $C_{12}H_{14}N_4O_2 \cdot H_2O$: C, 54.54; H, 6.10; N, 21.20. Found: C, 54.87; H, 6.00; N, 21.45.

(4) A mixture of the above object compound (3.35 g) of the Example 6-(3) and 100% hydrazin hydrate (33 ml) was heated at 120° for 2 hours under stirring and allowed to stand overnight at room temperature. The precipitate was collected by filtration, washed with methanol, and dried. The filtrate was evaporated in vacuo and the residue was triturated with ethanol to give the second crop. The combined crude products were recrystallized from 60% aqueous ethanol to give 6-(4-aminophenyl)-5-methyl-4,5-dihydro-1,2,4-triazin-3(2H)-one (1.61 g).

mp: 248° to 249.5° C.

NMR (DMSO-d$_6$, δ): 1.16 (3H, d, J=7 Hz), 4.52 (1H, d, q; J=3.5, 7 Hz), 5.41 (2H, s), 6.58 (2H, d, J=8 Hz), 7.23 (1H, b.s.), 7.42 (2H, d, J=8 Hz, 9.67 (1H, d, J=2 Hz).

Anal. Calcd. for $C_{10}H_{10}N_4O$: C, 58.81; H, 5.92; N, 27.44. Found: C, 58.64; H, 5.96; N, 27.33.

(5) A solution of sodium nitrite (3.6 g) in water (10 ml) was added dropwise to a solution of 6-(4-aminophenyl)-5-methyl-4,5-dihydro-1,2,4-triazin-3(2H)-one (9.8 g), concentrated hydrochloric acid (10 ml) and water (30 ml) at 0° C. After stirring for 0.5 hours, a solution of stannous chloride dihydrate (43.12 g) in conc. hydrochloric acid (43 ml) was added thereto at 0° C. After stirring for 2 hours, the mixture was made alkaline with an aqueous solution of sodium hydroxide and the resultant precipitates were collected by filtration and washed with water. The crude product was dissolved in 10% hydrochloric acid under warming, and then allowed to stand at room temperature. The precipitates were collected by filtration and then dissolved in water. The aqueous solution was washed with ethyl acetate, treated with activated charcoal, and made alkaline with an aqueous solution of sodium hydroxide. The resultant precipitates were collected by filtration, washed with water, and recrystallized from 10% hydrochloric acid to give 6-(4-hydrazinophenyl)-5-methyl-4,5-dihydro-1,2,4-triazin-3(2H)-one hydrochloride (3.2 g).

mp: 235° C. (dec.).

NMR (DMSO-d$_6$, δ): 1.19 (3H, d, J=7.5 Hz), 4.45 (1H; d, q; J=3, 7.5 Hz), 7.02 (2H, d, J=8.5 Hz), 7.26–7.50 (1H, b.m.), 7.65 (2H, d, J=8.5 Hz), 7.9–9.0 (1H, b.m.), 9.8–10.0 (1H, b.m.), 9.7–10.9 (2H, b.m.).

And further, 6-(4-hydrazinophenyl)-5-methyl-4,5-dihydro-1,2,4-triazine-3(2H)-one (1.35 g) was obtained by treating the above mother liquid with an aqueous solution of sodium hydroxide.

NMR (DMSO-d$_6$, δ): 1.19 (3H, d, J=7 Hz), 3.93–4.18 (2H, b.m.), 4.54 (1H, d, q: J=4, 7 Hz), 6.77 (2H, d, J=9 Hz), 6.95–7.14 (1H, b.m.), 7.14–7.34 (1H, b.m.), 7.49 (2H, d, J=9 Hz), 9.57–9.80 (1H, b.m.).

(6) A mixture of 6-(4-hydrazinophenyl)-5-methyl-4,5-dihydro-1,2,4-triazin-3(2H)-one (3.11 g) and 2-butanone (3.07 g) in ethanol (50 ml) and a saturated solution of hydrogen chloride in ethanol (1 drop) was refluxed for 2 hours with stirring. The mixture was filtered and the filtrate was evaporated in vacuo to give a residue. The residual solid was washed with ethyl acetate to give isomeric mixture of 6-(4-sec-butylidenehydrazinophenyl)-5-methyl-4,5-dihydro-1,2,4-triazin-3(2H)-one (3.12 g).

NMR (DMSO-d$_6$, δ): 1.05 (3H, t, J = 7.5Hz), 1.18 (3H, d, J = 7Hz), 1.86 (s), 1.92 (s) } (3H), 2.26 (q, J = 7.5), 2.34 (q, J = 7.5) } (2H), 4.55 (1H; d, q; J = 3, 7Hz), 7.07 (2H, d, J = 8.8Hz), 7.10–7.45 (1H, m), 7.56 (2H, d, J = 8.8Hz), 8.89 (s), 8.97 (s) } (1H), 9.64–9.83 (1H, m)

(7) A mixture of the above object compound (3.1 g) of (6) in ethylene glycol (20 ml) was refluxed for 13 hours with stirring and then allowed to room temperature. To the solution was added water and extracted with ethyl acetate. The extract was washed with water, dried over magnesium sulfate and chromatographed on silica gel (125 g) with ethyl acetate as an eluent. The eluates were evaporated and the residual solid was recrystallized from aqueous ethanol to give 6-(2,3-dimethylindol-5-yl)-5-methyl-4,5-dihydro-1,2,4-triazin-3(2H)-one (1.39 g).

mp: 292° to 296° C.

NMR (DMSO-d$_6$, δ): 1.25 (3H, d, J=6.5 Hz), 2.17 (3H, s), 2.31 (3H, s), 4.74 (1H; d, q; J=3.5, 6.5 Hz), 7.14–7.60 (3H, m), 7.67–7.80 (1H, m), 9.73–9.86 (1H, m), 10.66–10.90 (1H, m).

Anal. Calcd. for $C_{14}H_{16}N_4O$: C, 65.61; H, 6.25; N, 21.86. Found: C, 65.14; H, 6.17; N, 22.05.

EXAMPLE 7

(1) Methyl isothiocyanate (0.788 g) was added to a solution of 6-(4-aminophenyl)-5-methyl-4,5-dihydro-1,2,4-triazin-3(2H)-one (2 g) in N,N-dimethylformamide (20 ml) and the mixture was stirred for 4 hours at 110° C. After cooling, the mixture was treated with activated charcoal and evaporated in vacuo. The residual solid was washed with water and dried to give 6-[4-(3-methylthioureido)phenyl]-5-methyl-4,5-dihydro-1,2,4-triazin-3(2H)-one (2.7 g).

IR (Nujol): 3215, 3060, 1680, 1670 cm$^{-1}$.

NMR (DMSO-d$_6$, δ): 1.21 (3H, d, J=6.6 Hz), 2.53 (3H, d, J=2 Hz), 4.63 (1H; d, q; J=2, 6.6 Hz), 7.1–8.1 (6H, m), 9.68 (1H, b.s.), 9.91 (1H, b.s.).

(2) A mixture of the above obtained compound (1.5 g) of Example 7-(1) and thionyl chloride (7 ml) was heated at 50° for 4 hours with stirring and then evaporated in vacuo. To the residue was added 10% hydrochloric acid (30 ml), heated at 60° for 30 minutes, and filtered by suction. The filtrate was washed with chloroform and made alkaline with concentrated ammonium hydroxide under ice cooling. The resultant precipitate was collected by filtration washed with water, and recrystallized from a mixture of chloroform and methanol.

The above obtained product was purified by column chromatography on silica gel (40 g) with a mixture of chloroform and methanol (15:1) as an eluent to give 6-(2-methylaminobenzothiazol-6-yl)-5-methyl-4,5-dihydro-1,2,4-triazin-3(2H)-one (0.34 g).

mp: 290° to 295° C.

IR (Nujol): 3210, 3090, 1690 cm$^{-1}$.

NMR (DMSO-d$_6$, δ): 1.27 (3H, d, J=6.4 Hz), 2.98 (3H, d, J=4 Hz), 4.66 (1H, m), 7.41 (1H, b.s.), 7.43 (1H, d, J=8.8 Hz), 7.66 (1H; d, d; J=1.6, 8.8 Hz), 8.03 (1H, b.s.), 8.09 (1H, d, J=1.6 Hz), 9.91 (1H, b.s.).

Mass: m/e 275 (M+).

EXAMPLE 8

(1) To a stirred solution of 1-methyl-2-oxo-1,2,3,4-tetrahydroquinolin (17.7 g) and aluminum chloride (44.5 g) in 1,2-dichloroethane (26 ml) was added dropwise a solution of 2-phthalimidoacetyl chloride (25 g) in 1,2-dichloroethane (45 ml). The reaction mixture was stirred for 6 hours at 85° C. and then 22 hours at 60° C. After cooling, the mixture was poured into ice water and extracted with chloroform. The extract was washed successively with water, an aqueous solution of sodium bicarbonate and water, dried and evaporated. The residue was triturated with ethyl acetate and the resultant precipitates were collected by filtration, washed with ethyl acetate and dried to give 18.51 g of 1-methyl-2-oxo-6-phthalimidoacetyl-1,2,3,4-tetrahydroquinoline.

IR (Nujol): 1770 (s), 1720, 1685, 1600 cm$^{-1}$.

NMR (CDCl$_3$, δ): 2.4–3.2 (4H, m), 3.35 (3H, s), 5.07 (2H, s), 7.04 (1H, d; J=9.0 Hz), 7.5–8.1 (6H, m).

(2) A mixture of the above obtained compound (18.4 g) of Example 8-(1), conc. hydrochloric acid (36 ml) in acetic acid (72 ml) was refluxed for 6 hours. Conc. hydrochloric acid (72 ml) was added thereto and then further refluxed for 8.5 hours. After cooling, the reaction mixture was evaporated and triturated with ethanol. The resulting precipitates were collected by filtration, washed with ethanol and dried to give 9.12 g of 6-aminoacetyl-1-methyl-2-oxo-1,2,3,4-tetrahydroquinoline hydrochloride.

IR (Nujol): 3450, 3350, 1680, 1660, 1600 cm$^{-1}$.

NMR (DMSO-d$_6$, δ): 2.5–3.2 (4H, m), 3.26 (3H, s), 4.54 (2H, b.s.), 7.23 (1H, d, J=9.0 Hz), 7.8–8.13 (2H, m), 8.66 (2H, b.s.).

(3) To a stirred solution of the above obtained compound (4.0 g) in dichloromethane (40 ml) was added dropwise triethylamine (3.18 g) and then a solution of ethyl chloroformate (1.74 g) in dichloromethane (2 ml). After stirring for 20 minutes, the mixture was washed with diluted hydrochloric acid and brine, dried over magnesium sulfate, and evaporated. The residue was washed with diethyl ether to give 3.36 g of 6-ethoxycarbonylaminoacetyl-1-methyl-2-oxo-1,2,3,4-tetrahydroquinoline.

IR (Nujol): 3320, 1685 (shoulder), 1675, 1600 cm$^{-1}$.

NMR (DMSO-d$_6$, δ): 1.17 (3H, t, J=7 Hz), Ca. 2.5–3.2 (4H, m), 3.28 (3H, s), 4.02 (2H, q, J=7.0 Hz), 4.46 (2H, d, J=5.8 Hz), 7.1–7.4 (2H, m), 7.7–8.1 (2H, m).

(4) A mixture of the above obtained compound (2.98 g) of Example 8-(3), water (30 ml), ethanol (3 ml) and 100% hydrazine hydrate (5 ml) was refluxed for 15.5 hours. After cooling, resultant precipitates were collected by filtration, washed with water, and recrystallized from a mixture of N,N-dimethylformamide and water to give 1.74 g of 6-(1-methyl-2-oxo-1,2,3,4-tetrahydroquinolin-6-yl)-4,5-dihydro-1,2,4-triazin-3(2H)-one.

mp: 283° to 287° C. (dec.).

IR (Nujol): 3220, 3080, 1705, 1645 cm$^{-1}$.

NMR (DMSO-d$_6$, δ): 2.3–3.2 (4H, m), 3.26 (3H, s), 4.25 (2H, d, J=1.4 Hz), 7.06 (1H, d, J=9.2 Hz), 7.17 (1H, s), 7.4–7.6 (2H, m), 9.78 (1H, s).

Anal. Calcd. for C$_{13}$H$_{14}$N$_4$O$_2$: C: 60.46; H: 5.46; N: 21.69. Found: C: 60.31; H: 5.36; N: 21.73.

EXAMPLE 9

(1) 1-Methyl-2-indolinone (34.0 g) and 2-phthalimidoacetyl chloride (37.3 g) was reacted according to a similar manner to that of Example 8-(1). The object compound was purified by column chromatography on silica gel (300 g) using chloroform as an eluent to give 36.41 g of 1-methyl-5-phthalimidoacetyl-2-indolinone.

IR (Nujol): 1770 (small), 1720, 1675 cm$^{-1}$.

(2) 5-Aminoacetyl-1-methyl-2-indolinone hydrochloride (23.73 g) was obtained from the above object compound (36.0 g) of Example 9-(1) according to a similar manner to that of Example 8-(2).

IR (Nujol): 3150 (shoulder), 3000 (shoulder), 1720 (shoulder), 1710, 1680 cm$^{-1}$.

NMR (DMSO-d$_6$, δ): 3.17 (3H, s), 3.63 (2H, s), 4.2–4.8 (2H, m), 7.10 (1H, d, J=8.0 Hz), 7.7–8.1 (2H, m), 8.2–8.8 (2H, m).

(3) 5-Ethoxycarbonylaminoacetyl-1-methyl-2-indolinone (2.64 g) was obtained from the above object compound (4.8 g) of Example 9-(2) according to a similar manner to that of Example 8-(3).

IR (Nujol): 3350, 3270, 3160, 1635, 1610 cm$^{-1}$.

NMR (DMSO-d$_6$, δ): 1.17 (3H, t, J=6.4 Hz), 3.13 (3H, s), 3.59 (2H, s), 4.01 (2H, q, J=6.4 Hz), 4.45 (2H, d, J=6.0 Hz), 6.9–7.4 (2H, m), 7.8–8.1 (2H, m).

(4) 6-(1-Methyl-2-indolinon-5-yl)-4,5-dihydro-1,2,4-triazin-3(2H)-one (1.14 g) was obtained from the object compound (2.56 g) of Example 9-(3) according to a similar manner to that of Example 8-(4).

mp: >300° C. (recrystallized from a mixture of dimethylsulfoxide and methanol).

IR (Nujol): 3240, 3100, 1700, 1680 (shoulder).

NMR (DMSO-d$_6$, δ): 3.11 (3H, s), 3.55 (2H, s), 4.24 (2H, d, J=1.8), 6.95 (1H, d, J=8.6 Hz), 7.17 (1H, br. s), 7.4–7.7 (2H, m), 9.7–9.9 (1H, m)

EXAMPLE 10

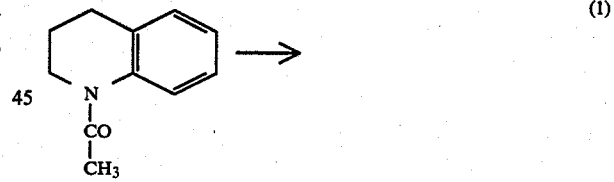

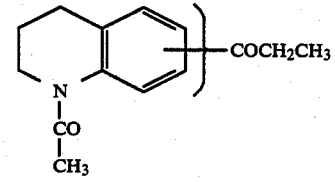

Propionyl chloride (67.2 g) was added dropwise to a mixture of 1-acetyl-1,2,3,4-tetrahydroquinoline (84 g) and aluminum chloride (169 g) over 1 hour with stirring, and the stirring was continued for 1 hour at room temperature and for 1.5 hours at 80° C. The mixture was dissolved in chloroform and then poured into ice water. The organic layer was separated, washed successively with water and an aqueous solution of sodium bicarbonate, dried over magnesium sulfate and evaporated. The oily residue was purified by column chromatography on silica gel (700 g) with a mixture of benzene and ethyl acetate (10:1) as an eluent to give an isomeric mixture of 6- and 7-propionyl-1-acetyl-1,2,3,4-tetrahydroquinoline (79.6 g).

NMR (CDCl₃, δ): 1.19 (3H, t, J=7 Hz), Ca. 1.7-2.3 (2H, m), 2.26 (3H, s), 2.80 (2H, t, J=6.2 Hz), 2.96 (2H, q, J=7 Hz), 3.79 (2H, t, J=6.6 Hz), 7.1-8.1 (3H, m).

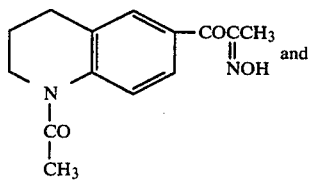 and

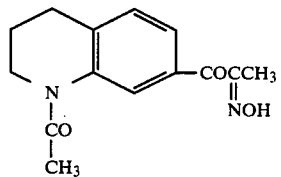

The above obtained isomeric mixture compound (79.5 g) was dissolved in methylene chloride (240 ml) and the solution was saturated with hydrogen chloride. To the stirred solution was added dropwise iso-amyl nitrite (48.4 g) over a period of 1 hour. After stirring for 30 minutes, the solution was evaporated in vacuo and the oily residue was dissolved in methanol (100 ml), and stirred for 1 hour. The resultant solid was collected by filtration and recrystallized from methanol to give 1-acetyl-6-(2-hydroxyiminopropionyl)-1,2,3,4-tetrahydroquinoline (17.97 g).

IR (Nujol): 3150, 3020, 1660, 1615, 1590 cm⁻¹.

NMR (DMSO-d₆, δ): Ca. 1.6-2.3 (2H, m), 2.01 (3H, s), 2.20 (3H, s), 2.75 (2H, t, J=6.4 Hz), 3.69 (2H, t, J=6 Hz), 7.64 (3H, s), 12.25 (1H, s).

The above obtained filtrates were evaporated in vacuo to give a residue. The residue was dissolved in 10% aqueous solution of sodium hydroxide and then washed with diethyl ether and then acidified with conc. hydrochloric acid. The resultant oil was extracted with chloroform, washed with water, dried and evaporated. The oily residue was chromatographed on silica gel (200 g) with a mixture of chloroform and ethyl acetate (10:1) as an eluent. The eluates were evaporated and the oily residue was triturated with diethyl ether to give 1-acetyl-7-(2-hydroxyiminopropionyl)-1,2,3,4-tetrahydroquinoline (22.67 g).

IR (Nujol): 3120, 3010 (shoulder), 1645, 1620, 1590 cm⁻¹.

NMR (DMSO-d₆, δ): Ca. 1.6-2.3 (2H, m), 2.01 (3H, s), 2.17 (3H, s), 2.76 (2H, t, J=6.6 Hz), 3.67 (2H, t, J=6.2 Hz), 7.25 (1H, d, J=7.8 Hz), 7.55 (1H, dd, J=1.8, 7.8 Hz), 7.98 (1H, d, J=1.8 Hz), 12.29 (1H, s).

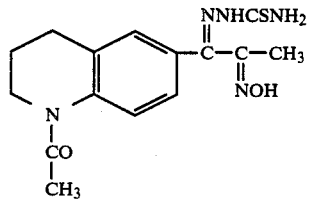

The above obtained 1-acetyl-6-(2-hydroxyiminopropionyl)-1,2,3,4-tetrahydroquinoline (17.5 g) was added to a suspension of thiosemicarbazide (6.2 g) in methanol (62 ml). To the solution was added saturated ethanolic solution of hydrogen chloride (1 ml), and then the mixture was refluxed for 40 minutes with stirring. After cooling, the resultant precipitates were collected by filtration, washed with methanol, and then dried to give 20.53 g of 1-(1-acetyl-1,2,3,4-tetrahydroquinolin-6-yl)-2-hydroxyimino-1-propanone thiosemicarbazone.

IR (Nujol): 3350, 3250, 3160, 1660, 1620 cm⁻¹.

| NMR (DMSO-d₆, δ): Ca. 1.7-2.1 (2H, m), |
| --- |
| 1.96 (s) } (3H), 2.19 (3H, s), <br> 2.19 (s) |
| 2.75 (2H, t, J = 6Hz), (2H, t, J = 6Hz), <br> 6.89-7.17 (1H, m), 7.43-7.79 (2H, m), |
| 8.1 (1H, b.s.), 8.53 (b.s.) } (2H), 11.73 (s) } (1H) <br> 10.63 (s) 12.12 (s) |

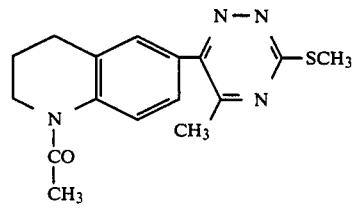

Sodium bicarbonate (10.15 g) and water (100 ml) were added to a suspension of the above obtained compound of Example 10-(3) (20.13 g) in methanol (100 ml). The mixture was refluxed for 6 hours with stirring and filtered by suction. To the filtrate was added dropwise methyl iodide (9.43 g), stirred for 30 minutes at room temperature, and concentrated to a small volume. The residue was extracted with ethyl acetate and the extract was washed with water, dried over magnesium sulfate, and evaporated in vacuo. The oily residue was purified by column chromatography on silica gel (120 g) with a mixture of benzene and ethyl acetate (5:1) as an eluent to give 6-(1-acetyl-1,2,3,4-tetrahydroquinolin-6-yl)-5-methyl-3-methylthio-1,2,4-triazine (13.86 g).

IR (film/NaCl): 1655 cm⁻¹.

NMR (DMSO-d₆, δ): Ca. 1.7-2.2 (2H, m), 2.21 (3H, s), 2.51 (3H, s), 2.63 (3H, s), 2.79 (2H, t, J=6.2 Hz), 3.74 (2H, t, J=6.4 Hz), Ca. 7.3-7.8 (3H, m).

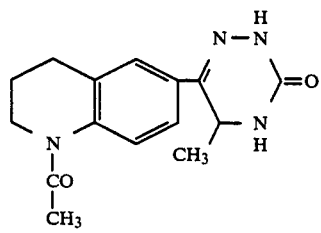

A mixture of the above obtained compound (11 g) of Example 10-(4) in 10% aqueous solution of potassium hydroxide (54 ml) and methanol (54 ml) was heated at 60° C. for 30 minutes with stirring and allowed at room temperature. To the solution was added sodium borohydride (2.65 g), stirred for 1.5 hours at room temperature and acidified with conc. hydrochloric acid. The resultant precipitates were collected by filtration, washed with water, dried, and recrystallized from 70% aqueous ethanol to give 6-(1-acetyl-1,2,3,4-tetrahydroquinolin-6-yl)-5-methyl-4,5-dihydro-1,2,4-triazin-3(2H)-one (6.19 g).

mp: 241° to 245° C.

IR (Nujol): 3200, 3080, 1685, 1645 cm$^{-1}$.

NMR (DMSO-d$_6$, δ): 1.22 (3H, d, J=7 Hz), Ca. 1.6–2.2 (2H, m), 2.21 (3H, s), 2.77 (2H, t, J=6.4 Hz), 3.72 (2H, t, J=6.4 Hz), 4.66 (1H; d,q; J=3.6, 7.0 Hz), 7.43 (1H, b.s.), 7.54 (3H, s), 9.95 (1H, d, J=1.2 Hz).

Anal. Calcd. for C$_{15}$H$_{18}$N$_4$O$_2$: C, 62.92; H, 6.34; N, 19.57. Found: C, 62.67; H, 6.31; N, 19.50.

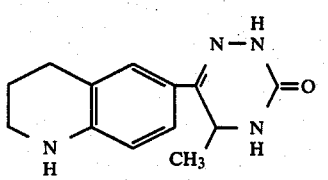
(6)

A suspension of the above obtained compound (5.32 g) of Example 10-(5) in 100% hydrazine hydrate (50 ml) was heated at 100° C. for 13 hours. After cooling, the resultant precipitates were collected by filtration, washed with methanol, dried and recrystallized from 70% aqueous ethanol to give crystals of 6-(1,2,3,4-tetrahydroquinolin-6-yl)-5-methyl-4,5-dihydro-1,2,4-triazin-3(2H)-one (4.27 g).

mp: 284° to 286° C.

IR (Nujol): 3400, 3200, 3060, 1685 cm$^{-1}$.

NMR (DMSO-d$_6$, δ): 1.16 (3H, d, J=6.6 Hz), 1.5–2.1 (2H, m), 2.68 (2H, t, J=6.2 Hz), 3.21 (2H, b.t, J=5.2 Hz), 4.48 (1H; d, q; J=2.6, 6.6 Hz), 6.02 (1H, b.s.), 6.41 (1H, d, J=8.4 Hz), 7.0.–7.4 (3H, m), 9.59 (1H, d, J=2 Hz).

Anal. Calcd. for C$_{13}$H$_{16}$N$_4$O: C, 63.92; H, 6.60; N, 22.93. Found: C, 63.92; H, 6.52; N, 22.85.

EXAMPLE 11

Synthesis of the compound of formula:

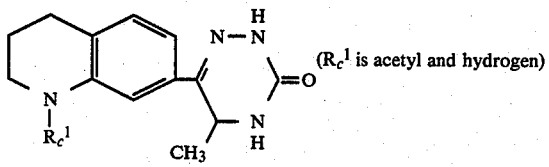
(R$_c^1$ is acetyl and hydrogen)

(1) 1-Acetyl-7-(2-hydroxyimino-1-thiosemicarbazonopropyl)-1,2,3,4-tetrahydroquinoline (22.03 g) was obtained from 1-acetyl-7-(2-hydroxyiminopropionyl)-1,2,3,4-tetrahydroquinoline (19.06 g) in a similar manner to that of Example 10-(3).

IR (Nujol): 3420, 3260, 3150, 1650, 1600 cm$^{-1}$.

NMR (DMSO-d$_6$, δ): Ca. 1.7–2.1 (2H, m), 1.97 (s) / 2.19 (s) } (3H), 2.19 (3H, s), 2.78 (2H, b.t., J = 6Hz), 3.72 (2H, t, J = 6Hz), Ca. 6.8–7.7 (3H, m), 8.09 (1H, b.s.), 8.56 (b.s.) / 10.72 (s) } (2H), 11.69 (s) / 12.18 (s) } (1H)

(2) The reaction of the above obtained compound (21.43 g) of Example 11-(1) with sodium bicarbonate and methyl iodide was carried out according to a similar manner to that of Example 10-(4). An isolation of the object compound was conducted as follows. The reaction mixture was evaporated to give a residue and extracted with ethyl acetate after addition of water. The extract was dried, evaporated and chromatographed on silica gel (80 g) with a mixture of benzene and ethyl acetate (5:1) as an eluent. The eluates were evaporated and the residue was triturated with methanol to give 6-(1-acetyl-1,2,3,4-tetrahydroquinolin-7-yl)-5-methyl-3-methylthio-1,2,4-triazine (9.29 g).

IR (Nujol): 1650 cm$^{-1}$.

NMR (DMSO-d$_6$, δ): Ca. 1.6–2.3 (2H, m), 2.23 (3H, s), 2.67 (3H, s), 2.83 (2H, t, J=6.8 Hz), 3.76 (2H, t, J=6 Hz), 7.38 (2H, b.s.), 7.82 (1H, b.s.).

(3) 6-(1-Acetyl-1,2,3,4-tetrahydroquinolin-7-yl)-5-methyl-4,5-dihydro-1,2,4-triazin-3(2H)-one (7.37 g) was obtained from the above obtained compound (8.98 g) of Example 11-(2) in a similar manner to that of Example 10-(5).

mp: 234° to 240° C. (dec.) (from aqueous ethanol).

IR (Nujol): 3340, 3280, 3150 (shoulder), 1705, 1690, 1610 cm$^{-1}$.

NMR (DMSO-d$_6$, δ): 1.21 (3H, d, J=6.8 Hz), Ca. 1.6–2.3 (2H, m), 2.18 (3H, s), 2.74 (2H, t, J=6.4 Hz), 3.73 (2H, t, J=7.2 Hz), 4.63 (1H, d, q; J=3.6, 6.8 Hz), 7.21 (1H, d, J=8.2 Hz), Ca. 7.4 (1H, b.s.), 7.49 (1H; d,d; J=1.8, 8.2 Hz), 7.86 (1H, d, J=1.8 Hz), 10.0 (1H, b.s.).

Anal. Calcd. for C$_{15}$H$_{18}$N$_4$O$_2$: C, 62.92; H, 6.34; N, 19.57. Found: C, 62.85; H, 6.30; N, 19.50.

(4) 6-(1,2,3,4-Tetrahydroquinolin-7-yl)-5-methyl-4,5-dihydro-1,2,4-triazin-3(2H)-one (4.36 g) was obtained from the above obtained compound (7.19 g) of Example 11-(3) according to a similar manner to that of Example 10-(6).

mp: 231° to 238° C. (from 70% aqueous ethanol).

IR (Nujol): 3420, 3210, 3090, 1695 cm$^{-1}$.

NMR (DMSO-d$_6$, δ): 1.18 (3H, d, J=6.6 Hz), 1.5–2.1 (2H, m), 2.66 (2H, t, J=6.2 Hz), 3.19 (2H, b.t., J=6 Hz), 4.48 (1H; d, q; J=3.4, 6.6 Hz), 5.68 (1H, b.s.), 6.6–7.0 (3H, m), 7.30 (1H, b.s.), 9.83 (1H; d, J=1.8 Hz).

Anal. Calcd. for C$_{13}$H$_{16}$N$_4$O: C, 63.92; H, 6.60; N, 22.93. Found: C, 63.64; H, 6.53; N, 22.89.

EXAMPLE 12

Synthesis of the compound of the formula:

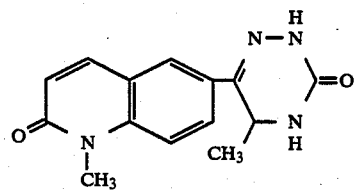

(1) A solution of 1-methyl-2-oxo-6-propionyl-1,2,3,4-tetrahydroquinoline (20 g) and 2,3-dichloro-5,6-dicyano-1,4-benzoquinone (20.9 g) in benzene (250 ml) was refluxed for 1 day. The mixture was filtered by suction and evaporated. The residue was chromatographed on silica gel (400 g) with a mixture of benzene and ethyl acetate (1:1) as an eluent. The eluates were concentrated to give an oil of 1-methyl-2-oxo-6-propionyl-1,2-dihydroquinoline (7.72 g).

(2) 6-(1-Methyl-2-oxo-1,2-dihydroquinolin-6-yl)-5-methyl-3-methylthio-1,2,4-triazine (1.19 g) was obtained from the above obtained compound (7.44 g) of Example 12-(1) according to a similar manner to that of Example 10-(2), (3) and (4).

NMR (CDCl$_3$, δ): 2.63 (3H, s), 2.74 (3H, s), 3.79 (3H, s), 6.77 (1H, d, J=9.5 Hz), 7.50 (1H, d, J=8.5 Hz), 7.64-8.06 (3H, m).

(3) 6-(1-Methyl-2-oxo-1,2-dihydroquinolin-6-yl)-5-methyl-4,5-dihydro-1,2,4-triazin-3(2H)-one (0.71 g) was obtained from the above obtained compound (1.19 g) of Example 12-(2) in a similar manner to that of Example 10-(5).

mp: 293° to 296° C. (from aqueous ethanol)

NMR (DMSO-d$_6$, δ): 1.24 (3H, d, J=6.5 Hz), 3.63 (3H, s), 4.72 (1H; d, q; J=3, 6.5 Hz), 6.64 (1H, d, J=10 Hz), 7.35-7.67 (2H, m), 7.86-8.16 (3H, m), 9.98-10.13 (1H, m).

Anal. Calcd. for C$_{14}$H$_{14}$N$_4$O$_2$: C, 62.21; H, 5.22; N, 20.73. Found: C, 62.22; H, 5.19; N, 20.86.

EXAMPLE 13

Synthesis of the compound of the formula:

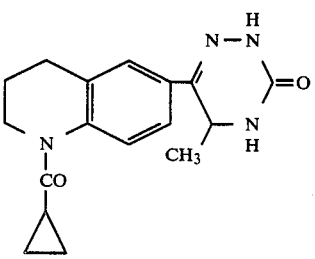

Cyclopropanecarbonyl chloride (0.47 g) was added dropwise to a stirred solution of 6-(1,2,3,4-tetrahydroquinolin-6-yl)-5-methyl-4,5-dihydro-1,2,4-triazin-3(2H)-one (0.73 g) and triethylamine (0.6 g) in N,N-dimethylformamide (7.3 ml) under ice cooling and the stirring was continued for 30 minutes. The solution was evaporated in vacuo and the residue was dissolved in chloroform. The solution was washed with diluted hydrochloric acid, dried, and evaporated. The residue was chromatographed on silica gel (5 g) using chloroform and then a mixture of chloroform and methanol (20:1) as an eluents. The eluates were evaporated in vacuo and the oily residue was crystallized from ethanol to give 6-(1-cyclopropanecarbonyl-1,2,3,4-tetrahydroquinolin-6-yl)-5-methyl-4,5-dihydro-1,2,4-triazin-3(2H)-one (0.26 g).

mp: 215° to 219° C. (dec.).

IR (Nujol): 3210, 3090, 1700, 1655 cm$^{-1}$.

NMR (DMSO-d$_6$, δ): Ca. 0.6-1.2 (4H, m), 1.23 (3H, d, J=7 Hz), 1.7-2.2 (3H, m), 2.78 (2H, t, J=6.4 Hz), 3.76 (2H, t, J=6.4 Hz), 4.63 (1H; d, q; J=3, 7 Hz), 7.40 (1H, b.s.), 7.50 (3H, b.s.), 9.91 (1H, d, J=1.8 Hz).

EXAMPLE 14

Synthesis of the compound of the formula:

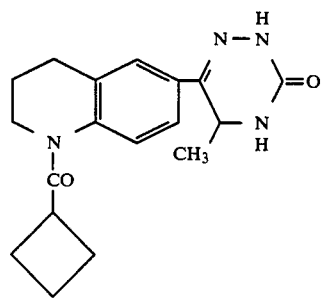

6-(1-Cyclobutanecarbonyl-1,2,3,4-tetrahydroquinolin-6-yl)-5-methyl-4,5-dihydro-1,2,4-triazin-3(2H)-one (0.45 g) was obtained from 6-(1,2,3,4-tetrahydroquinolin-6-yl)-5-methyl-4,5-dihydro-1,2,4-triazin-3(2H)-one (0.6 g) in a similar manner to that of Example 13.

mp: 247° to 251° C. (from 70% aqueous ethanol).

IR (Nujol): 3210, 3080, 1693, 1655 cm$^{-1}$.

NMR (DMSO-d$_6$, δ): 1.21 (3H, d, J=6.6 Hz), 1.5-2.5 (6H, m), 2.5-3.0 (4H, m), 3.40 (1H, m), 3.66 (2H, m), 4.65 (1H, m), 7.3-7.7 (3H, m), 7.42 (1H, b.s.), 9.95 (1H, b.s.).

Anal. Calcd. for C$_{18}$H$_{22}$N$_4$O$_2$: C, 66.24; H, 6.79; N, 17.17. Found: C, 66.16; H, 6.85; N, 17.01.

EXAMPLE 15

Synthesis of the compound of the formula:

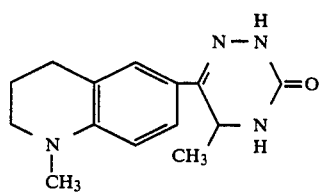

Sodium cyanoborohydride (0.19 g) was added portionwise to a suspension of 6-(1,2,3,4-tetrahydroquinolin-6-yl)-5-methyl-4,5-dihydro-1,2,4-triazin-3(2H)-one (0.74 g), 36% aqueous formaldehyde (0.34 ml), acetic acid (1 ml) and methanol (3 ml) at room temperature. After stirring for 0.5 hours at the same temperature, the resultant precipitates were collected by filtration, washed with methanol, dried, and recrystallized from 70% aqueous ethanol to give 0.66 g of 6-(1-methyl-1,2,3,4-tetrahydroquinolin-6-yl)-5-methyl-4,5-dihydro-1,2,4-triazin-3(2H)-one.

mp: >255° C. (dec.).

IR (Nujol): 3200, 3080, 1690 cm$^{-1}$.

NMR (DMSO-d$_6$, δ): 1.17 (3H, d, J=6.4 Hz), 1.6-2.2 (2H, m), Ca. 2.5-2.9 (2H, m), 2.85 (3H, s), 3.1-3.4 (2H, m), 4.3-4.8 (1H, m), 6.53 (1H, d, J=9.8 Hz), 7.1-7.5 (3H, m), 9.63 (1H, b.s.).

EXAMPLE 16

Synthesis the compound of the formula:

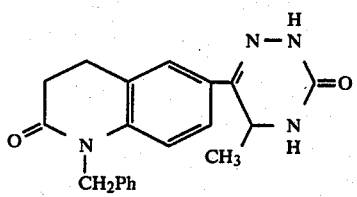

(1) 1-Benzyl-6-(2-hydroxyiminopropionyl)-2-oxo-1,2,3,4-tetrahydroquinoline (5.45 g) was obtained from 1-benzyl-6-propionyl-2-oxo-1,2,3,4-tetrahydroquinoline (11.62 g) according to a similar manner to that of Example 10-(2).

IR (Nujol): 3160 (broad), 1645, 1595 cm$^{-1}$.

NMR (CDCl$_3$, δ): 2.13 (3H, s), 2.4–3.2 (4H, m), 5.13 (2H, s), 6.85 (1H, d, J=9.6 Hz), 7.1–7.5 (5H, m), 7.6–7.9 (2H, m), 8.93 (1H, b.s.).

(2) 1-Benzyl-6-(2-hydroxyimino-1-thiosemicarbazonopropyl)-2-oxo-1,2,3,4-tetrahydroquinoline (6.73 g) (isomeric mixture) was obtained from the above object compound (5.31 g) of Example 16-(1) according to a similar manner to that of Example 10-(3).

IR (Nujol): 3400, 3240, 3130, 1655, 1600 cm$^{-1}$.

NMR (DMSO-d$_6$, δ): 1.91 (s), 2.1 (s) } (3H), Ca. 2.7–3.1 (4H, m), 5.16 (2H, s), 6.8–7.8 (8H, m), 8.13 (1H, b.s.), 8.5 (2H, b.s.), 12.13 (s), 11.73 (s) } (1H)

(3) 6-(1-Benzyl-2-oxo-1,2,3,4-tetrahydroquinolin-6-yl)-5-methyl-3-methylthio-1,2,4-triazine (2.49 g) was obtained from the above object compound (6.6 g) of Example 16-(2) according to a similar manner to that of Example 10-(4).

NMR (CDCl$_3$, δ): 2.51 (3H, s), 2.66 (3H, s), Ca. 2.7–3.3 (4H, m), 5.22 (2H, s), 6.97 (1H, d, J=8.4 Hz), 7.1–7.6 (7H, m).

(4) 6-(1-Benzyl-2-oxo-1,2,3,4-tetrahydroquinolin-6-yl)-5-methyl-4,5-dihydro-1,2,4-triazin-3(2H)-one (0.92 g) was obtained from the above object compound (2.34 g) of Example 16-(3) according to a similar manner to that of Example 10-(5).

mp: 219° to 223° C. (from methanol).

IR (Nujol): 3200, 3080, 1705, 1685 cm$^{-1}$.

NMR (DMSO-d$_6$, δ): 1.17 (3H, d, J=6.6 Hz), Ca. 2.6–3.3 (4H, m), 4.59 (1H; d, q; J=3, 6.6 Hz), 5.16 (2H, s), 6.90 (1H, d, J=8.8 Hz), Ca. 7.1–7.8 (8H, m), 9.90 (1H, d, J=1.6 Hz).

EXAMPLE 17

Synthesis the compound of the formula:

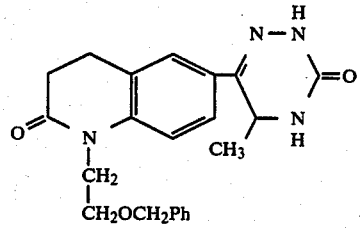

(1) 1-(2-Benzyloxyethyl)-6-(2-hydroxyiminopropionyl)-2-oxo-1,2,3,4-tetrahydroquinoline (9.19 g) was obtained from 1-(2-benzyloxyethyl)-6-propionyl-2-oxo-1,2,3,4-tetrahydroquinoline (32.4 g) according to a similar manner to that of Example 10-(2).

IR (Nujol): 3250 (shoulder), 3160, 3020, 1640, 1600 cm$^{-1}$.

NMR (CDCl$_3$, δ): 2.15 (3H, s), 2.3–3.1 (4H, m), 3.70 (2H, t, J=5.5 Hz), 4.14 (2H, t, J=5.5 Hz), 4.47 (2H, s), 7.0–7.5 (6H, m), 7.7–8.0 (2H, m), Ca. 10.0 (1H, b.s.).

(2) 1-(2-Benzyloxyethyl)-6-(2-hydroxyimino-1-thiosemicarbazonopropyl)-2-oxo-1,2,3,4-tetrahydroquinoline (8.99 g) (isomeric mixture) was obtained from the above object compound (8.98 g) of Example 17-(1) according to a similar manner to that of Example 10-(3).

IR (Nujol): 3410, 3300, 3160, 1665, 1600 cm$^{-1}$.

NMR (DMSO-d$_6$, δ): 1.96 (s), 2.17 (s) } (3H), Ca. 2.4–3.1 (4H, m), 3.63 (2H; b.t., J = 5Hz), 4.15 (2H; b.t., J = 5Hz), 4.47 (s), 4.50 (s) } (2H), 6.92–7.5 (3H, m), 7.3 (5H, s),

Ca. 8.0 (b.s.), 7.66 (b.s.) } (1H), 8.13 (b.s.), 8.54 (b.s.) } (2H), 12.1 (s), 11.69 (s) } (1H)

(3) 6-[1-(2-Benzyloxyethyl)-2-oxo-1,2,3,4-tetrahydroquinolin-6-yl]-3-methylthio-5-methyl-1,2,4-triazine (6.81 g) was obtained from the above object compound (10.1 g) of Example 17-(2) according to a similar manner to that of Example 10-(4).

IR (film/NaCl): 1675, 1610 cm$^{-1}$.

NMR (CDCl$_3$, δ): 2.59 (3H, s), 2.72 (3H, s), Ca. 2.5–3.2 (4H, m), 3.79 (2H, t, J=5.2 Hz), 4.23 (2H, t, J=5.2 Hz), 4.56 (2H, s), 7.29 (5H, s), 7.3–7.7 (3H, m).

(4) 6-[1-(2-Benzyloxyethyl)-2-oxo-1,2,3,4-tetrahydroquinolin-6-yl]-5-methyl-4,5-dihydro-1,2,4-triazin-3(2H)-one (3.92 g) was obtained from the above object compound (6.62 g) of Example 17-(3) according to a similar manner to that of Example 10-(5).

IR (Nujol): 3220, 3100, 1685, 1645, 1620 cm$^{-1}$.

NMR (DMSO-d$_6$, δ): 1.21 (3H, d, J=6.4 Hz), Ca. 2.4–2.8 (2H, m), 2.8–3.2 (2H, m), 3.62 (2H, t, J=5.4 Hz), 4.13 (2H, t, J=5.4 Hz), 4.48 (2H, s), Ca. 4.4–4.9 (1H, m), Ca. 7.1–7.8 (4H, m), 7.26 (5H, s), 9.93 (1H, d, J=2 Hz).

EXAMPLE 18

Synthesis the compound of the formula:

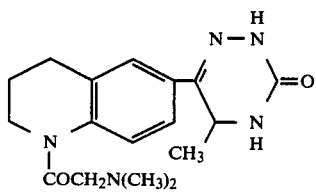

6-(1-Dimethylaminoacetamido-1,2,3,4-tetrahydroquinolin-6-yl)-5-methyl-4,5-dihydro-1,2,4-triazin-3(2H)-one (0.42 g) was obtained by reacting the object compound (0.7 g) of Example 10-(6) with 2-dimethylaminoacetyl chloride hydrochloride (0.771 g) according to a similar manner to that of Example 13.

mp: 239° to 246° C.

IR (Nujol): 3200, 3100, 1690, 1655 cm$^{-1}$.

NMR (DMSO-d$_6$, δ): 1.20 (3H, d, J=6.8 Hz), Ca. 1.5–2.3 (2H, m), 2.21 (6H, s), 2.76 (2H, b.t., J=7 Hz), 3.29 (2H, s), 3.75 (2H, b.t., J=6.6 Hz), 4.62 (1H; d, q; J=3.6, 6.8 Hz), 7.40 (1H, br s), Ca. 7.4–7.8 (3H, m), 9.91 (1H, d, J=2 Hz).

Anal. Calcd. for C$_{17}$H$_{23}$N$_5$O$_2$: C, 61.99; H, 7.04; N, 21.26. Found: C, 61.73; H, 6.94; N, 21.30.

EXAMPLE 19

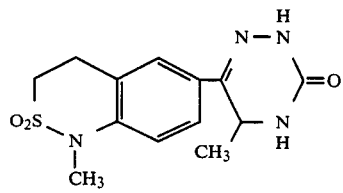

(1) 6-(2-Hydroxyiminopropionyl)-1-methyl-3,4-dihydro-1H-2,1-benzothiazine 2,2-dioxide (2.6 g) was obtained from 1-methyl-6-propionyl-3,4-dihydro-1H-2,1-benzothiazine 2,2-dioxide (5.1 g) according to a similar manner to that of Example 4-(1).

mp: 178° to 180° C.

IR (Nujol): 3440, 1650, 1330, 1155, 1145 cm$^{-1}$.

NMR (DMSO-d$_6$, δ): 2.04 (3H, s), 3.00–3.68 (4H, m), 3.27 (3H, s), 7.16 (1H, d, J=8.5 Hz), 7.79 (1H, br s), 7.83 (1H, dd, J=8.5 Hz, 2 Hz), 12.34 (1H, s).

(2) 6-(2-Hydroxyimino-1-thiosemicarbazonopropyl)-1-methyl-3,4-dihydro-1H-2,1-benzothiazine 2,2-dioxide (2.70 g) was obtained from the reaction product of Example 19-(1) (2.50 g) according to a similar manner to that of Example 1-(1).

mp: 227° C. (dec.).

IR (Nujol): 3460, 3340, 3125, 1610, 1340, 1155 cm$^{-1}$.

NMR (DMSO-d$_6$, δ): 3.23 (3H, s), 3.32–3.80 (4H, m), 7.00–10.67 (6H, m), $\left. \begin{array}{l} 1.95\ (s) \\ 2.12\ (s) \end{array} \right\}$ 3H, $\left. \begin{array}{l} 11.72\ (s) \\ 12.12\ (s) \end{array} \right\}$ 1H (3) 6-(5-Methyl-3-methylthio-1,2,4-triazin-6-yl)-1-methyl-3,4-dihydro-1H-2,1-benzothiazine 2,2-dioxide (1.20 g) was obtained from the reaction product of Example 19-(2) (2.10 g) according to a similar manner to that of Example 4-(3).

mp: 162° to 164° C. (recrystallized from ethyl acetate).

IR (Nujol): 1345, 1160 cm$^{-1}$.

NMR (DMSO-d$_6$, δ): 2.50 (3H, s), 2.62 (3H, s), 3.27 (3H, s), 3.45–3.70 (4H, m), 7.20 (1H, d, J=8 Hz), 7.57 (1H, d, J=2 Hz), 7.62 (1H, dd, J=2 Hz, 8 Hz).

(4) 6-(5-Methyl-3-oxo-2,3,4,5-tetrahydro-1,2,4-triazin-6-yl)-1-methyl-3,4-dihydro-1H-2,1-benzothiazine 2,2-dioxide (1.40 g) was obtained from the reaction product of Example 19-(3) (1.60 g) according to a similar manner to that of Example 4-(4).

mp: 291° to 293° C. (recrystallized from a mixture of ethanol and N,N-dimethylformamide).

IR (Nujol): 3225, 3075, 1700, 1350, 1165, 1130 cm$^{-1}$.

NMR (DMSO-d$_6$, δ): 1.23 (3H, d, J=7 Hz), 3.24 (3H, s), 3.27–3.64 (4H, m), 4.54–4.77 (1H, m), 7.12 (1H, d, J=9 Hz), 7.43 (1H, br s), 7.61 (1H, br s), 7.64 (1H, d, J=9 Hz), 9.96 (1H, d, J=2 Hz).

Anal Calcd. for C$_{13}$H$_{16}$N$_4$O$_3$S: C, 50.64; H, 5.23; N, 18.17. Found: C, 50.50; H, 5.36; N, 18.11.

EXAMPLE 20

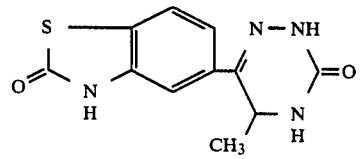

(1) 5-(2-Hydroxyiminopropionyl)benzothiazolin-2-one (22.0 g) was obtained from 5-propionylbenzothiazolin-2-one (20.0 g) according to a similar manner to that of Example 4-(1).

mp: 238° to 240° C.

IR (Nujol): 3625, 3525, 3280, 3225, 3170, 1710 (sh), 1660 cm$^{-1}$.

NMR (DMSO-d$_6$, δ): 2.05 (3H, s), 7.18 (1H, d, J=8 Hz), 7.82 (1H, dd, J=8 Hz, 2 Hz), 8.10 (1H, d, J=2 Hz), 12.23 (1H, br s), 12.33 (1H, s).

(2) 5-(2-Hydroxyimino-1-thiosemicarbazonopropyl)-benzothiazolin-2-one (2.70 g) was obtained from the reaction product of Example 20-(1) (3.00 g) according to a similar manner to that of Example 1-(1).

mp: 244° C. (dec.).

IR (Nujol): 3340, 3260, 3175, 1710, 1670, 1620 cm$^{-1}$.

NMR (DMSO-d$_6$, δ): 7.03–8.58 (5H, m), 12.00 (1H, br s), 2.00 (s) and 2.18 (s) (3H, 1:2), 8.80 (s) and 10.62 (s) (1H, 2:1), 11.68 (s) and 12.18 (s) (1H, 2:1).

(3) 5-(5-Methyl-3-methylthio-1,2,4-triazin-6-yl)benzothiazolin-2-one (5.80 g) was obtained from the reaction product of Example 20-(2) (16.8 g) according to a similar manner to that of Example 4-(3) provided that 1,8-diazabicyclo[5,4,0]undec-7-ene was used instead of potassium carbonate.

mp: 242° to 244° C.

IR (Nujol): 3180, 1675, 1640 cm$^{-1}$.

NMR (DMSO-d$_6$, δ): 2.63 (3H, s), 7.25 (1H, d, J=8 Hz), 7.60 (1H, dd, J=8 Hz, 2 Hz), 7.90 (1H, d, J=2 Hz), 12.00 (1H, br s).

(4) 5-(5-Methyl-3-oxo-2,3,4,5-tetrahydro-1,2,4-triazin-6-yl)benzothiazolin-2-one (4.75 g) was obtained from the reaction product of Example 20-(3) (5.70 g) according to a similar manner to that of Example 4-(4).

mp: 336° to 338° C. (recrystallized from a mixture of N,N-dimethylformamide and ethanol).

IR (Nujol): 3230, 3090, 2700, 1720 (sh), 1690 cm$^{-1}$.

NMR (DMSO-$d_6$, δ): 1.25 (3H, d, J=7 Hz), 4.58–4.85 (1H, m), 7.26 (1H, d, J=9 Hz), 7.53 (1H, s), 7.79 (1H, dd, J=9 Hz, 2 Hz), 8.04 (1H, d, J=2 Hz), 10.09 (1H, d, J=2 Hz).

Anal. Calcd. for $C_{11}H_{10}N_4O_2S$: C, 50.37; H, 3.84; N, 21.36. Found: C, 50.75; H, 3.91; N, 21.42.

EXAMPLE 21

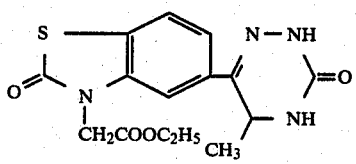

Ethyl bromoacetate (0.67 ml) was added dropwise to a stirred solution of the object compound of Example 20-(4) (1.50 g) and potassium carbonate (0.83 g) in N,N-dimethylformamide (100 ml), and the stirring was continued for 2.5 hours at ambient temperature. The reaction mixture was evaporated in vacuo and the residue was dissolved in ethyl acetate and water. The organic layer was separated, washed with brine, dried over magnesium sulfate and evaporated to give 1.80 g of 3-ethoxycarbonylmethyl-5-(5-methyl-3-oxo-2,3,4,5-tetrahydro-1,2,4-triazin-6-yl)benzothiazolin-2-one.

mp: 200° to 202° C. (recrystallized from acetone).

IR (Nujol): 3230, 3190, 1748, 1710, 1690 cm$^{-1}$.

NMR (DMSO-$d_6$, δ): 1.22 (3H, t, J=8 Hz), 1.24 (3H, d, J=8 Hz), 4.18 (2H, q, J=8 Hz), 4.48–4.72 (1H, m), 4.86 (2H, s), 7.34 (1H, d, J=9 Hz), 7.43 (1H, s), 7.74 (1H, dd, J=9 Hz, 2 Hz), 8.06 (1H, d, J=2 Hz), 10.00 (1H, d, J=2 Hz).

Anal. Calcd. for $C_{15}H_{16}N_4O_4S$ C, 51.72; H, 4.63, N, 16.08. Found: C, 51.65; H, 4.55; N, 16.07.

EXAMPLE 22

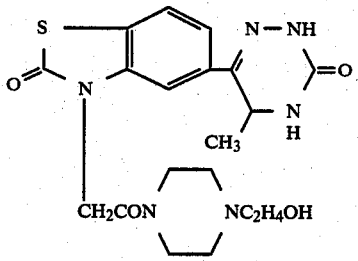

A mixture of the object compound of Example 21 (1.0 g) and 1-(2-hydroxyethyl)piperazine (1.2 g) was stirred for 4 hours at 120° C. After cooling, the reaction mixture was chromatographed on silica gel (45 g) by eluting with a mixture of chloroform and methanol (9:1) to give 0.9 g of 3-[4-(2-hydroxyethyl)piperazin-1-yl-carbonylmethyl]-5-(5-methyl-3-oxo-2,3,4,5-tetrahydro-1,2,4-triazin-6-yl)benzothiazolin-2-one.

mp: 248° to 250° C. (recrystallized from ethanol).

IR (Nujol): 3500, 3225, 3100, 1690, 1670, 1635 cm$^{-1}$.

NMR (DMSO-$d_6$, δ): 1.24 (3H, d, J=8 Hz), Ca. 2.2–2.8 (4H, m), 3.32–3.79 (8H, m), 4.39 (1H, t, J=5 Hz), 4.52–4.74 (1H, m), 4.93 (2H, s), 7.17 (1H, d, J=8 Hz), 7.43 (1H, br s), 7.72 (1H, dd, J=8 Hz, 2 Hz), 8.01 (1H, d, J=2 Hz), 9.98 (1H, d, J=2 Hz).

Anal. Calcd. for $C_{19}H_{24}N_6O_4S$: C, 52.77; H, 5.59; N, 19.43. Found: C, 52.66; H, 5.77; N, 19.19.

EXAMPLE 23

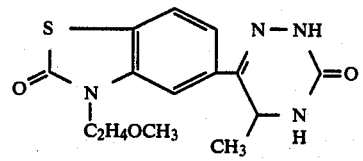

3-(2-Methoxyethyl)-5-(5-methyl-3-oxo-2,3,4,5-tetrahydro-1,2,4-triazin-6-yl)benzothiazolin-2-one (0.63 g) was obtained from the object compound of Example 20-(4) (0.70 g) and 2-bromoethyl methyl ether (0.25 ml) according to a similar manner to that of Example 21.

mp: 178° to 180° C. (recrystallized from ethyl acetate).

IR (Nujol): 3225, 3075, 1700, 1685 cm$^{-1}$.

NMR (DMSO-$d_6$, δ): 1.17 (3H, d, J=7 Hz), 3.31 (3H, s), 3.62 (2H, t, J=5 Hz), 4.15 (2H, t, J=5 Hz), 4.46–4.89 (1H, m), 7.38 (1H, d, J=8 Hz), 7.45 (1H, s), 7.73 (1H, dd, J=8 Hz, 2 Hz), 8.01 (1H, d, J=2 Hz), 10.01 (1H, d, J=2 Hz).

EXAMPLE 24

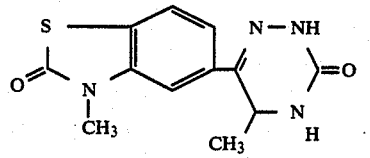

3-Methyl-5-(5-methyl-3-oxo-2,3,4,5-tetrahydro-1,2,4-triazin-6-yl)benzothiazolin-2-one (0.50 g) was obtained from the object compound of Example 20-(4) (0.70 g) and methyl iodide (0.17 ml) according to a similar manner to that of Example 21.

mp: 251° to 253° C.

IR (Nujol): 3220, 3080, 1700, 1680 cm$^{-1}$.

NMR (DMSO-$d_6$, δ): 1.23 (3H, d, J=7 Hz), 3.40 (3H, s), 4.47–4.85 (1H, m), 7.29 (1H, d, J=9 Hz), 7.43 (1H, s), 7.75 (1H, dd, J=9 Hz, 2 Hz), 8.00 (1H, d, J=2 Hz), 10.00 (1H, d, J=2 Hz).

Anal. Calcd. for $C_{12}H_{12}N_4O_2S$: C, 52.16; H, 4.38; N, 20.28. Found: C, 51.21; H, 4.56; N, 19.92.

EXAMPLE 25

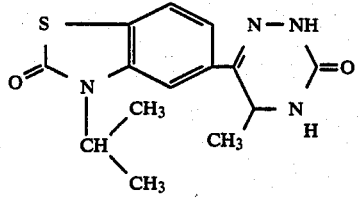

3-Isopropyl-5-(5-methyl-3-oxo-2,3,4,5-tetrahydro-1,2,4-triazin-6-yl)benzothiazolin-2-one (0.38 g) was obtained from the object compound of Example 20-(4) (0.80 g) and isopropyl iodide (0.30 ml) according to a similar manner to that of Example 21.

mp: 214° to 216° C. (recrystallized from a mixture of ethanol and n-hexane).

IR (Nujol): 3225, 3080, 1710, 1690, 1670 cm$^{-1}$.

NMR (DMSO-d$_6$, δ): 1.23 (3H, d, J=7 Hz), 1.50 (6H, d, J=7 Hz), 4.48–5.03 (2H, m), 7.43 (1H, br s), 7.50 (1H, d, J=8.5 Hz), 7.74 (1H, dd, J=8.5 Hz, 2 Hz), 8.02 (1H, d, J=2 Hz), 10.02 (1H, d, J=2 Hz).

Anal. Calcd. for $C_{14}H_{16}N_4O_2S$: C, 55.25; H, 5.30; N, 18.41. Found: C, 55.38; H, 5.23; N, 18.57.

What is claimed is:

1. A compound of the formula

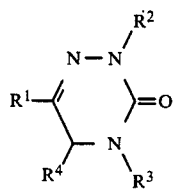

wherein $R^1$ is a 1,2,3,4-tetrahydroquinolyl which may be substituted with a lower alkyl, lower alkanoyl, cyclic lower alkanoyl or lower alkylamino(lower)alkanoyl, 2-oxo-1,2,3,4-tetrahydroquinolyl which may be substituted with a lower alkyl, benzyl, benzyloxy(lower)alkyl or hydroxy (lower alkyl), 2-oxo-1,2-dihydroquinolyl which may be substituted with a lower alkyl, indolyl which may be substituted with up to 2 lower alkyls, 2-oxoindolinyl which may be substituted with a lower alkyl, benzothiazolyl which may be substituted with a lower alkylamino, 2-oxobenzothiazolinyl which may be substituted with a lower alkyl, lower alkoxy(lower)alkyl, lower alkoxycarbonyl (lower) alkyl or 4-(2-hydroxyethyl) piperazin-1-yl-carbonylmethyl, 3,4-dihydro-1H-2,1-benzothiazinyl which may be substituted with a lower alkyl in which the S atom being optionally oxidized, or 3-oxo-2,3-dihydro-4H-1,4-benzoxazinyl which may be substituted with a lower alkyl;

$R^2$ is a hydrogen, lower alkenyl, benzyl, carboxy(lower)alkyl or lower alkoxycarbonyl(lower)alkyl;

$R^3$ and $R^4$, which may be the same or different, are each hydrogen or lower alkyl or together represent a bond;

provided that when $R^1$ is 2-oxo-1,2,3,4-tetrahydroquinolyl which is unsubstituted or substituted by a lower alkyl, then, $R^4$ is a hydrogen or $R^2$ is a lower alkenyl, benzyl, carboxy(lower)alkyl or lower alkoxycarbonyl(lower)alkyl; and pharmaceutically acceptable salt thereof.

2. A compound of claim 1, wherein $R^1$ is a 1,2,3,4-tetrahydroquinolyl which may be substituted with a; lower alkyl, lower alkanoyl, cyclic lower alkanoyl or lower alkylamino(lower)alkanoyl.

3. A compound of claim 1, wherein $R^1$ is a 2-oxo-1,2,3,4-tetrahydroquinolyl which is substituted with a lower alkyl and $R^2$ is a lower alkenyl, benzyl, carboxy(lower)alkyl or lower alkoxycarbonyl(lower)alkyl.

4. A compound of claim 1, wherein $R^1$ is a 2-oxo-1,2,3,4-tetrahydroquinolyl which is substituted with a lower alkyl and $R^2$, $R^3$ and $R^4$ are each hydrogen.

5. The compound according to claim 4, which is 6-(1-methyl-2-oxo-1,2,3,4-tetrahydroquinolin-6-yl)-4,5-dihydro-1,2,4-triazin-3(2H)-one.

6. A compound of claim 1, wherein $R^1$ is a 2-oxo-1,2,3,4-tetrahydroquinolyl which is substituted with a hydroxy(lower)alkyl.

7. A compound of claim 1, wherein $R^1$ is a 2-oxo-1,2-dihydroquinolyl which may be substituted with a lower alkyl.

8. The compound according to claim 7, which is 6-(1-methyl-2-oxo-1,2-dihydroquinolin-6-yl)-5-methyl-4,5-dihydro-1,2,4-triazin-3(2H)-one.

9. A compound of claim 1, wherein $R^1$ is a indolyl which may be substituted with up to two lower alkyl(s).

10. A compound of claim 1, wherein $R^1$ is a 2-oxoindolinyl which may be substituted with a lower alkyl.

11. A compound of claim 1, wherein $R^1$ is a benzothiazolyl which may be substituted with a lower alkylamino.

12. A compound of claim 1, wherein $R^1$ is a 2-oxobenzothiazolinyl which may be substituted with a; lower alkyl, lower alkoxy(lower)alkyl, lower alkoxycarbonyl(lower)alkyl or 4-(2-hydroxyethyl)piperazin-1-yl-carbonylmethyl.

13. A compound of claim 1, wherein $R^1$ is a 3,4-dihydro-1H-2,1-benzothiazinyl in which the S atom being optionally oxidized.

14. A compound of claim 1, wherein $R^1$ is a 3-oxo-2,3-dihydro-4H-1,4-benzoxazinyl which may be substituted with a lower alkyl.

15. An antihypertensive pharmaceutical composition comprising an antihypertensive effective amount of a compound of claim 1 for treating hypertension.

16. An antithrombotic pharmaceutical composition comprising an antithrombotic effective amount of a compound of claim 1 for treating thrombosis.

17. An antiulcerative pharmaceutical composition comprising an antiulcerative effective amount of a compound of claim 1 for treating ulcer.

18. A method for treating hypertension which comprises administering an antihypertensive effective amount of a compound of claim 1 to a subject in need of treatment.

19. A method for treating thrombosis which comprises administering an antithrombotic effective amount of a compound of claim 1 to a subject in need of treatment.

20. A method for treating ulcer which comprises administering an antiulcerative effective amount of a compound of claim 1 to a subject in need of treatment.

* * * * *